US011643438B2

(12) United States Patent
Cichewicz et al.

(10) Patent No.: US 11,643,438 B2
(45) Date of Patent: May 9, 2023

(54) ANTIMICROBIAL PEPTIDES AND METHODS OF USE

(71) Applicant: The Board of Regents of the University of Oklahoma, Norman, OK (US)

(72) Inventors: Robert H. Cichewicz, Norman, OK (US); Lin Du, Norman, OK (US); Jianlan You, Norman, OK (US); Allison O. Mattes, Avondale, AZ (US); Shikha Srivastava, Norman, OK (US); Saikat Haldar, Debipur (IN)

(73) Assignee: The Board of Regents of the University of Oklahoma, Norman, OK (US)

(*) Notice: Subject to any disclaimer, the term of this patent is extended or adjusted under 35 U.S.C. 154(b) by 0 days.

(21) Appl. No.: 17/260,148

(22) PCT Filed: Jul. 19, 2019

(86) PCT No.: PCT/US2019/042563
§ 371 (c)(1),
(2) Date: Jan. 13, 2021

(87) PCT Pub. No.: WO2020/018888
PCT Pub. Date: Jan. 23, 2020

(65) Prior Publication Data
US 2021/0317167 A1 Oct. 14, 2021

Related U.S. Application Data

(60) Provisional application No. 62/701,079, filed on Jul. 20, 2018.

(51) Int. Cl.
*C07K 11/02* (2006.01)
*A61P 31/10* (2006.01)
(52) U.S. Cl.
CPC .............. *C07K 11/02* (2013.01); *A61P 31/10* (2018.01)
(58) Field of Classification Search
CPC .................................. C07K 11/02; A61P 31/10
See application file for complete search history.

(56) References Cited

U.S. PATENT DOCUMENTS

| | | |
|---|---|---|
| 5,057,493 A | 10/1991 | Takesako et al. |
| 5,158,876 A | 10/1992 | Takesako et al. |
| 5,200,505 A | 4/1993 | Takesako et al. |
| 5,260,214 A | 11/1993 | Takesako et al. |
| 5,633,345 A | 5/1997 | Kurome et al. |
| 5,633,346 A | 5/1997 | Kurome et al. |
| 5,677,423 A | 10/1997 | Rodriguez |
| 5,698,670 A | 12/1997 | Kurome et al. |
| 5,795,909 A | 8/1998 | Shashoua et al. |
| 5,976,866 A | 11/1999 | Heidier et al. |
| 6,001,815 A | 12/1999 | Yanai et al. |
| 6,015,689 A | 1/2000 | Okado et al. |
| 6,022,684 A | 2/2000 | Radding et al. |
| 6,022,949 A | 2/2000 | Okado et al. |
| 6,043,051 A | 3/2000 | Okado |
| 6,194,166 B1 | 2/2001 | Okado et al. |
| 6,252,041 B1 | 6/2001 | Yanai et al. |
| 6,267,957 B1 | 7/2001 | Green et al. |
| 6,294,651 B1 | 9/2001 | Okado et al. |
| 6,316,406 B1 | 11/2001 | Yanai et al. |
| 6,348,577 B1 | 2/2002 | Okado et al. |
| 6,432,664 B1 | 8/2002 | Okado et al. |
| 6,576,636 B2 | 6/2003 | Webb et al. |
| 6,602,902 B2 | 8/2003 | Shashoua et al. |
| 6,693,174 B2 | 2/2004 | Okado et al. |
| 6,743,780 B1 | 6/2004 | Hanak et al. |
| 6,808,892 B1 | 10/2004 | Schnell et al. |
| 6,919,076 B1 | 7/2005 | Green |
| 6,958,148 B1 | 10/2005 | Green et al. |
| 7,109,018 B1 | 9/2006 | Yanai et al. |
| 7,199,151 B2 | 4/2007 | Shashoua et al. |
| 7,214,664 B2 | 5/2007 | Mitra et al. |
| 7,351,739 B2 | 4/2008 | Ho et al. |
| 7,459,268 B2 | 12/2008 | Kitamura et al. |
| 7,569,553 B2 | 8/2009 | Krieg |
| 7,605,138 B2 | 10/2009 | Krieg |

(Continued)

FOREIGN PATENT DOCUMENTS

EP 0581429 A3 10/1993
WO 1995018147 A1 7/1995

OTHER PUBLICATIONS

Aeed et al, Inhibition of Inositol Phosphorylceramide Synthase by the Cyclic Peptide Aureobasidin A, Antimicrobial Agents and Chemotherapy, 2009, 53, pp. 496-504.*
Kalkanci et al, Ocular Fungal Infections, Current Eye Research, 2011, 36, pp. 179-189.*
Mattes, Allison; "Advancement of Natural Products: Optimization of Instrumentation and Examples of Their Application to the Isolation of New Compounds," A Dissertation Approved for the Department of Chemistry and Biochemistry, University of Oklahoma (2019) 198 pages.
PubChem-CID-56672239, Create Date: Mar. 6, 2012, entire document.
Tiberghien, et al; "Aureobasidins: Structure-Activity Relationships for the inhibition of the Human MDR1 P-Glycoprotein ABC-Transporter"; J. Med.Chem (2000), vol. 43, pp. 2547-2556.

(Continued)

*Primary Examiner* — Li N Komatsu
(74) *Attorney, Agent, or Firm* — Dunlap Codding, P.C.

(57) ABSTRACT

Cyclic depsipeptide-class molecules, referred to herein as persephacins (including analogs thereof), having similarities to aureobasidin A, are described. The persephacins have antimicrobial activity, such as antifungal activity against a diverse range of clinically-relevant fungal pathogens, antiprotozoan parasite activity, and antibacterial activity, and can be used for example in treatments of difficult-to-treat ocular fungal infections at lower concentrations than natamycin. The active compounds may be combined with a secondary compound in a composition.

3 Claims, 13 Drawing Sheets
(9 of 13 Drawing Sheet(s) Filed in Color)

(56) References Cited

U.S. PATENT DOCUMENTS

| | | | |
|---|---|---|---|
| 7,659,088 B2 | 2/2010 | Eihammer |
| 7,807,803 B2 | 10/2010 | Krieg |
| 7,910,553 B2 | 3/2011 | Mitra et al. |
| 8,058,238 B2 | 11/2011 | Kelleher et al. |
| 8,129,342 B2 | 3/2012 | Kelleher et al. |
| 8,178,650 B2 | 5/2012 | Krastel et al. |
| 8,232,265 B2 | 7/2012 | Rogers et al. |
| 8,263,125 B2 | 9/2012 | Vaya et al. |
| 8,314,077 B2 | 11/2012 | Webb et al. |
| 8,343,962 B2 | 1/2013 | Kisak et al. |
| 8,513,304 B2 | 8/2013 | Kisak et al. |
| 8,604,164 B2 | 12/2013 | Kelleher et al. |
| 8,614,289 B2 | 12/2013 | Acemoglu et al. |
| 8,618,292 B2 | 12/2013 | Palladino et al. |
| 8,637,469 B2 | 1/2014 | Levitt |
| 8,697,069 B2 | 4/2014 | Kuchroo et al. |
| 8,697,638 B2 | 4/2014 | Keith et al. |
| 8,741,942 B2 | 6/2014 | Cuny et al. |
| 8,796,224 B2 | 8/2014 | Keith et al. |
| 8,802,596 B2 | 8/2014 | Rogers et al. |
| 8,846,610 B2 | 9/2014 | Keith et al. |
| 8,853,357 B2 | 10/2014 | Kelleher et al. |
| 8,877,204 B2 | 11/2014 | Srivastava et al. |
| 8,883,720 B2 | 11/2014 | Gombert et al. |
| 8,906,848 B2 | 12/2014 | Wuts et al. |
| 8,987,413 B2 | 3/2015 | Acemoglu et al. |
| 9,062,094 B2 | 6/2015 | Rau et al. |
| 9,067,978 B2 | 6/2015 | Acemoglu et al. |
| 9,169,504 B2 | 10/2015 | Anzai et al. |
| 9,278,134 B2 | 3/2016 | Rogers et al. |
| 9,278,997 B2 | 3/2016 | Acemoglu et al. |
| 9,308,162 B2 | 4/2016 | Norton |
| 9,308,181 B2 | 4/2016 | Kisak et al. |
| 9,493,512 B2 | 11/2016 | Acemoglu et al. |
| 2003/0083240 A1 | 5/2003 | Finn et al. |
| 2006/0194714 A1 | 8/2006 | Finn et al. |
| 2007/0082878 A1 | 4/2007 | Romero et al. |
| 2008/0119395 A1 | 5/2008 | Finn et al. |
| 2008/0227765 A9 | 9/2008 | Romero et al. |
| 2009/0156472 A1 | 6/2009 | Krastel et al. |
| 2010/0056434 A1 | 3/2010 | Packham et al. |
| 2010/0056435 A1 | 3/2010 | Ganesan et al. |
| 2011/0092437 A1 | 4/2011 | Krastel et al. |
| 2011/0112090 A1 | 5/2011 | Shuttleworth et al. |
| 2011/0201550 A1 | 8/2011 | Harder et al. |
| 2011/0262969 A1 | 10/2011 | Harder |
| 2012/0196790 A1 | 8/2012 | Krastel et al. |
| 2012/0277406 A1 | 11/2012 | Acemoglu et al. |
| 2013/0172267 A1 | 7/2013 | Krastel et al. |
| 2014/0024578 A1* | 1/2014 | Wuts ............... A61P 31/10 530/323 |
| 2014/0080995 A1 | 3/2014 | Acemoglu et al. |
| 2014/0100353 A1 | 4/2014 | Acemoglu et al. |
| 2014/0100355 A1 | 4/2014 | Acemoglu et al. |
| 2015/0141615 A1 | 5/2015 | Acemoglu et al. |
| 2015/0218224 A1 | 8/2015 | Acemoglu et al. |
| 2017/0022254 A1 | 1/2017 | Acemoglu et al. |
| 2017/0183382 A1 | 6/2017 | Piscopio et al. |
| 2018/0016304 A1 | 1/2018 | Hauser et al. |
| 2019/0177372 A1 | 6/2019 | Piscopio et al. |
| 2020/0031871 A1 | 1/2020 | Hughes et al. |
| 2020/0282016 A1 | 9/2020 | Curtis et al. |
| 2020/0347097 A1 | 11/2020 | Piscopio et al. |

OTHER PUBLICATIONS

International Search Report, dated Oct. 2, 2019, in PCT/US2019/42563, filed Jul. 19, 2019.

Written Opinion of the International Searching Authority, dated Oct. 2, 2019, in PCT/US2019/42563, filed Jul. 19, 2019.

Sivanathan, et al.; "Cyclodepsipeptides: A Rich Source of Biologically Active Compounds for Drug Research," Molecules (2014), vol. 19, pp. 12368-12420.

Ota, et al.; "One-Step Catalytic Asymmetric Synthesis of all-syn Deoxypropionate Motif from Propylene: Total Synthesis of (2R,4R6R,8R)-2,4,6,8-tetramethyidecanoic Acid," PNAS (2016) vol. 113, No. 11, pp. 2857-2861.

Kaur, et al.; "Total Synthesis of the Cyclic Depsipeptide YM-280193, a Platelet Aggregation Inhibitor," Org. Lett. (2015) vol. 17, pp. 492-495.

\* cited by examiner

*Candida albicans*
SC5314

Negative control

50 µg/ml

125 µg/ml

250 µg/ml 1 mg/ml

*Candida albicans*
SC5314 FluR

Negative control

50 µg/ml

125 µg/ml

250 µg/ml 1 mg/ml

*Aspergillus fumigatus*
NRRL5109

Negative control

50 µg/ml

125 µg/ml

250 µg/ml 1 mg/ml

*Candida albicans*
SC5314
Clinical dosage 0.1% 118A

2% Fluconazole

5% Natamycin

NC

*Candida albicans*
SC5314 FluR

Clinical dosage 0.1% 118A

2% Fluconazole

5% Natamycin

NC

*Aspergillus fumigatus*
NRRL5109

Clinical dosage 0.1% 118A

2% Fluconazole

5% Natamycin

NC

ANTIMICROBIAL PEPTIDES AND METHODS OF USE

CROSS-REFERENCE TO RELATED APPLICATIONS

This application is a US National Stage Application under 35 USC § 371 of International Application No. PCT/US2019/42563, filed Jul. 19, 2019; which claims benefit under 35 U.S.C. 119(e) of U.S. Provisional Application Ser. No. 62/701,079, filed Jul. 20, 2018, the entirety of which is hereby expressly incorporated herein by reference.

BACKGROUND

Global surveys of drug resistance have raised alarm that humans are losing the upper hand in the fight against microbial pathogens. While most of the discussions surrounding these concerns have focused on the looming challenges posed by bacteria, it is critical to note that fungi continue to take a substantial toll on human morbidity and mortality and, furthermore, drug resistance among new and existing fungal pathogens is on the rise. The challenges posed by fungi are compounded by the fact that clinicians have a meager repertoire of four classes of antifungal agents at their disposal: azoles (e.g., ergosterol biosysnthesis inhibitors), polyenes (e.g., for interaction and disruption of fungal membrane sterols), pyrimidine analogs (e.g., inhibitors of DNA synthesis), and echinocandins (e.g., inhibitors of 1,3-β glucan synthase). With so few treatment options available, the rapid rise of new and drug-resistant fungal pathogens (e.g., *Candida auris, Candida glabrata, Aspergillus fumigatus, Aspergillus terreus, Scedosporium* spp., and *Fusarium* spp.) has resulted in a steadily increasing number of incurable fungal infections. Failure to address this problem is certain to have catastrophic consequences for patients; consequently, there is an urgent need to identify new antifungal agents that exploit yet unutilized mechanisms of action against a growing number of threatening fungal pathogens. It is to addressing this need that the compounds and methods of the present disclosure are directed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Several embodiments of the present disclosure are hereby illustrated in the appended drawings. It is to be noted however, that the appended drawings only illustrate several typical embodiments and are therefore not intended to be considered limiting of the scope of the present disclosure.

DETAILED DESCRIPTION

Figure 1:
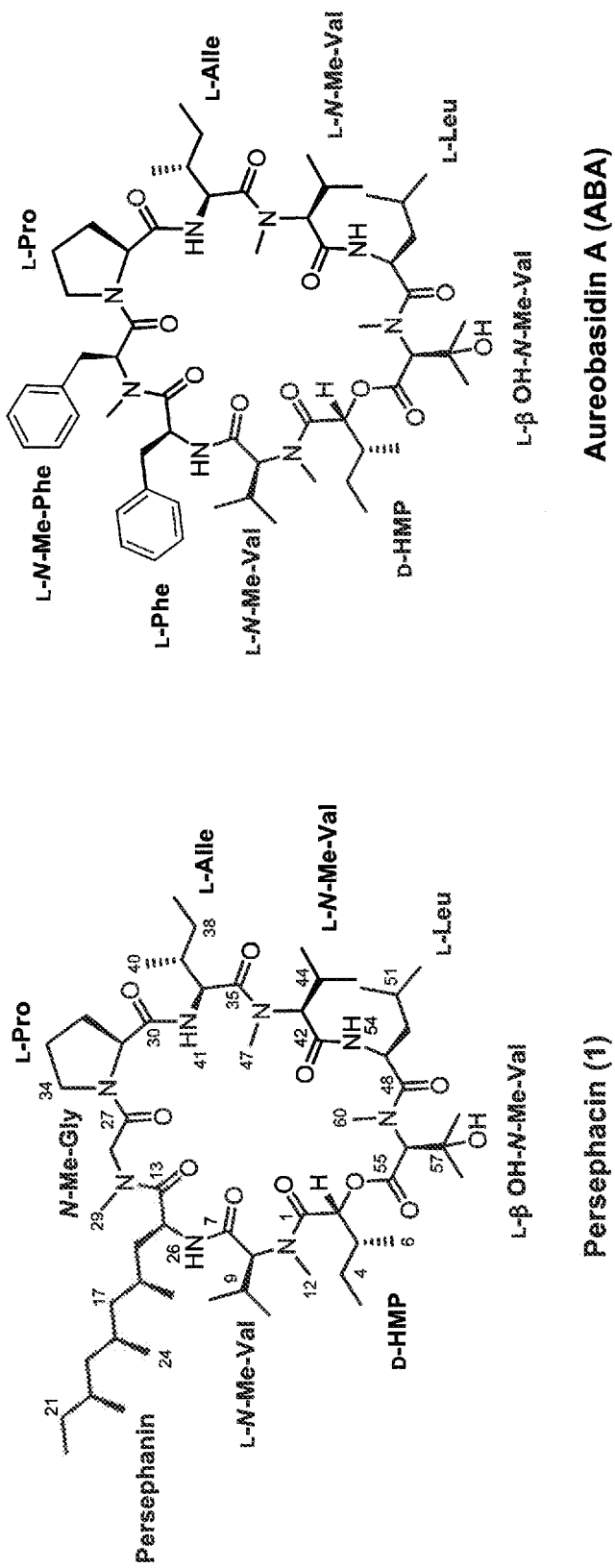
FIG. 1 shows chemical structures of persephacin A (Compound 1) and aureobasidin A (ABA).

The novel compounds of the present disclosure, new cyclic depsipeptide-class molecules referred to herein as persephacins and that have similarities to aureobasidin A (ABA), have been shown herein to have antimicrobial activity, such as antifungal activity against a diverse range of clinically-relevant fungal pathogens, antiprotozoan parasite activity, and antibacterial activity; in addition, these novel compounds can be used as antimicrobial (e.g., antifungal) treatments.

Natural products have been an important source of antimicrobial drugs, which offer a wide variety of novel structural skeletons that operate using new modes of action. A variety of plant samples were gathered from the areas surrounding Norman, Okla., U.S.A. with a focus on securing slow-growing fungi (characterized as isolates that became visible to the naked eye after a prolonged (e.g., 3-4 weeks) period of time), as well as fungi that upon emerging from plant tissues, exhibited signs of inhibiting neighboring fungal colonies. In the course of these efforts, one of the slow-to-emerge fungi exhibited a remarkable ability to forestall the growth of the surrounding fungal colonies. This unusual isolate, which was obtained from a sample of *Poplar* sp. leaf, was subsequently identified as a probable *Elsinoë* sp. (Synonym: *Sphaceloma* sp.), and the fungus was subsequently shown to be the source of a metabolite that was capable of causing broad-spectrum growth inhibition against a wide variety of other endophytic isolates. Bioassay-guided fractionation performed on extracts prepared from the *Elsinoë* sp. isolate led to the identification of the new depsipeptide, designated herein as persephacin (also referred to herein as persephacin A, compound 1, and compound 118A), which contains a new amino acid residue having a hydrocarbon side chain (designated herein as persephanine (Compound 9)).

Persephacin (1) is a fascinating addition to the small, yet promising family of antifungal natural products that features an ABA-like depsipetide scaffold. Unlike other naturally occurring ABA analogs, compound 1 exhibits broad spectrum antifungal activity against a wide array of pathogenic yeast and filamentous fungi, including (but not limited to) Aspergilli. In particular, the present disclosure describes steps taken to determine the structure of the new antifungal natural product, as well as offer evidence demonstrating the metabolite's remarkable range of antifungal activity against a diverse set of clinically-relevant fungal pathogens. Examples of yeast and filamentous fungi that the presently disclosed active agents can be used in treatments against include, but are not limited to, strains of *Candida albicans, Candida glabrata, Candida parapsilosis, Candida kefyr, Candida krusei, Candida auris, Candida duobushaemulonii, Candida haemulonii, Kodameae ohmeri, Candida lusitaniae, Saccharomyces cerevisiae, Candida tropicalis, Cryptococcus neoformans, Aspergillus fumigatus, Aspergillus flavus, Aspergillus niger, Aspergillus terreus, Curvularia lunata, Rhizopus oryzae, Mucor circinelloides, Fusarium solani, Paecilomyces lilacinus*, and *Hamigera insecticola*, for example as shown in Tables 1-3.

Before further describing various embodiments of the compounds, compositions, and methods of the present disclosure in more detail by way of exemplary description, examples, and results, it is to be understood that the compounds, compositions, and methods of the present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning, and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications, and equivalents apparent to those having ordinary skill in the art are included within the scope of the present disclosure. Thus, while the compounds, compositions, and methods of the present disclosure have been described in terms of particular embodiments, it will be apparent to those of skill in the art that variations may be applied to the compounds, compositions, and/or methods and in the steps or in the sequence of steps of the methods described herein without departing from the concept, spirit, and scope of the inventive concepts.

All patents, published patent applications, and non-patent publications mentioned in the specification or referenced in any portion of this application, including (but not limited to) U.S. Ser. No. 62/701,079, filed Jul. 20, 2018, are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities, and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example. By way of further example, the range 1 wt % to 99 wt % is intended to include any sub-range therein, although that sub-range may not be explicitly designated herein. For example, since the range 1 wt % to 99 wt % includes all integers from 1 to 99, the sub-ranges therein include any range having a minimum value of 1 wt % to 98 wt % and any maximum value of 2 wt % to 99 wt %, such as but not limited to, 5 wt % to 75 wt %, 10 wt % to 50 wt %, or 15 wt % to 40 wt %.

As used in this specification and claims, the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" and "approximately" are used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately," where used herein when referring to a measurable value such as an amount, a temporal duration, and the like, is meant to encompass, for example, variations of ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment. Further, all references to one or more embodiments or examples are to be construed as non-limiting to the claims.

The term "pharmaceutically acceptable" refers to compounds and compositions which are suitable for administration to humans and/or animals without undue adverse side effects such as toxicity, irritation, and/or allergic response commensurate with a reasonable benefit/risk ratio. The compounds of the present disclosure may be combined with one or more pharmaceutically-acceptable excipients, including carriers, vehicles, and diluents which may improve solubility, deliverability, dispersion, stability, and/or conformational integrity of the compounds or conjugates thereof.

As used herein, "pure" or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 50% (w/w) pure, or at least 55% (w/w) pure, or at least 60% (w/w) pure, or at least 65% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure. Where used herein "% (w/w)" is used interchangeably with "wt %." Where used herein "% purity" generally refers to the total % of the one or more persephacins (i.e., persephacin and persephacin analogues) in a mixture or extract.

The terms "subject" and "patient" are used interchangeably herein and will be understood to refer to a warm blooded animal, particularly a mammal. Non-limiting examples of animals within the scope and meaning of this term include dogs, cats, rabbits, rats, mice, guinea pigs, chinchillas, horses, goats, cattle, sheep, zoo animals, Old and New World monkeys, non-human primates, and humans, and any other animal susceptible to a fungal condition, or other condition susceptible to treatment with the presently disclosed compounds and compositions as described herein.

"Treatment" refers to treatment of a condition. "Prevention" refers to prophylactic or preventative treatment measures or reducing the onset of the condition. The term "treating" refers to administering the composition to a subject for treatment of the condition. The treatment may be therapeutic, for example in the case wherein the toxicity of the agent can be harmful.

The terms "therapeutic composition" and "pharmaceutical composition" refer to a persephacin-containing and/or persephacin analogue-containing composition that may be administered to a subject by any method known in the art or otherwise contemplated herein, wherein administration of the composition brings about treatment of a condition such as is described elsewhere herein. In addition, the compositions of the present disclosure, which may contain one or more secondary compounds, may be designed to provide delayed, controlled, extended, and/or sustained release using formulation techniques which are well known in the art.

The term "effective amount" refers to an amount of a persephacin compound which is sufficient to exhibit a detectable anti-fungal or other therapeutic effect against a condition in a subject without excessive adverse side effects (such as substantial toxicity, irritation, and allergic response) commensurate with a reasonable benefit/risk ratio when used in the manner of the present disclosure. The effective amount for a subject will depend upon the subject's type, size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

More particularly, an effective amount of a persephacin compound of the present disclosure refers to an amount which is effective in controlling, reducing, or inhibiting a condition as described herein, such as (but not limited to) a fungal infection. The term "controlling" is intended to refer to all processes wherein there may be a slowing, interrupting, arresting, or stopping of the progression of the condition and does not necessarily indicate a total elimination of the symptoms of the condition. In at least one embodiment the persephacin compound is effective in controlling, reducing, or inhibiting the effects of a condition, such as an infection by, but not limited to, any of the fungi described herein.

The term "effective amount" is further meant to define an amount resulting in the improvement of any parameters or clinical symptoms characteristic of a condition. The actual dose will vary with the patient's overall condition, the seriousness of the condition or symptoms, and counter indications. As used herein, the term "effective amount" also means the total amount of each active agent (component) of the pharmaceutical composition or method that is sufficient to show a meaningful patient benefit, i.e., reduction of a condition. When applied to an individual active ingredient, administered alone, the term refers to that ingredient alone. When applied to a combination, the term refers to combined amounts of the active agent(s) that results in the therapeutic effect, whether administered in combination, serially or simultaneously.

The term "ameliorate" means a detectable or measurable improvement in a subject's condition or symptom thereof. A detectable or measurable improvement includes a subjective or objective decrease, reduction, inhibition, suppression, limit, or control in the occurrence, frequency, severity, progression, or duration of the condition, or an improvement in a symptom or an underlying cause or a consequence of the condition, or a reversal of the condition. A successful treatment outcome can lead to a "therapeutic effect" or "benefit" of ameliorating, decreasing, reducing, inhibiting, suppressing, limiting, controlling, or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most, or all adverse symptoms, complications, consequences, or underlying causes associated with the condition. Thus, a satisfactory endpoint may be achieved when there is an incremental improvement such as a partial decrease, reduction, inhibition, suppression, limit, control, or prevention in the occurrence, frequency, severity, progression, or duration, or inhibition or reversal of the condition (e.g., stabilizing), over a short or long duration of time (e.g., seconds, minutes, hours).

The term "alkyl" means a straight or branched hydrocarbon group having 1-20 carbon atoms and includes, for example, methyl, ethyl, n-propyl, isopropyl, n-butyl, sec-butyl, isobutyl, tert.-butyl, n-pentyl, n-hexyl, n-heptyl, n-octyl, n-nonyl, n-decyl, fluoromethyl, fluorochloromethyl, and trifluoromethyl, and the like. Alkyl groups may be optionally substituted with one or more substituents, such as (but not limited to) halogens. The term "branched" should be understood to represent a linear straight chain hydrocarbon group having one or more lower alkyl groups, such as (but not limited to) methyl, ethyl, or propyl, attached to it. The term "alkenyl" refers to an alkyl group containing at least one carbon-carbon double bond. Alkenyl groups may be optionally substituted with one or more substituents. The term "alkynyl" refers to an alkyl group containing at least one carbon-carbon triple bond. Alkynyl groups may be optionally substituted with one or more substituents. The term "halogen" (or "halo") should be understood to include fluoro (fluorine), chloro (chlorine), bromo (bromine), and iodo (iodine). The term "hydroxypropyl" refers to three-carbon groups comprising one hydroxyl group and includes, but is not limited to, 2-hydroxypropyl and 1-hydroxypropan-2-yl. The term "dihydroxypropyl" refers to three-carbon groups comprising two hydroxyl groups and includes, but is not limited to, 1,3-dihydroxypropan-2-yl and 2,3-dihydroxypropyl.

The disclosed compounds may exist in various stereoisomeric forms. Stereoisomers are compounds that differ only in their spatial arrangement. Enantiomers are pairs of stereoisomers that are non-superimposable mirror images of one another, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms. Stereoisomers of the compounds of the present disclosure may be structural isomers (e.g., constitutional) and/or optical isomers (e.g., configurational, including geometric, diastereomeric, and enantiomeric isomers).

Turning now to particular examples of compounds (active agents) of the present disclosure, in one non-limiting embodiment, the active agent is persephacin (also referred to in results below as 118A and persephacin A), the structural formula of which is shown below as Compound 1:

Compound 1

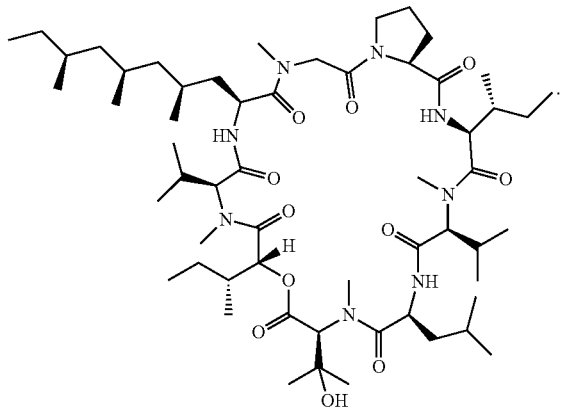 [SMILES: CC[C@H](C)C[C@H](C)C[C@H](C)C[C@@H]1NC(=O)[C@H](C(C)C)N(C)C(=O)[C@@H]([C@H](C)CC)OC(=O)[C@H](C(C)(C)O)N(C)C(=O)[C@H](CC(C)C)NC(=O)[C@H](C(C)C)N(C)C(=O)[C@H]([C@H](C)CC)NC(=O)[C@@H]2CCCN2C(=O)CN(C)C1=O]

In another non-limiting embodiment, the present disclosure is directed to the class of compounds (active agents) represented by Structural Formula I and stereoisomers thereof:

I

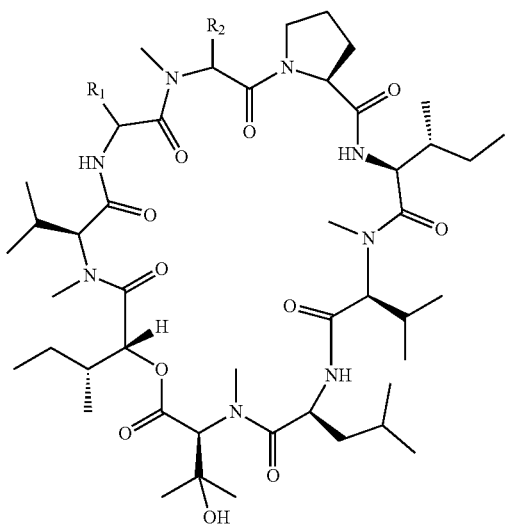

wherein $R_1$ and $R_2$ are independently selected from the group consisting of hydrogen (H), deuterium (D), an amino acid side chain, a linear or branched alkyl ($C_2$-$C_{20}$), a linear or branched alkenyl ($C_2$-$C_{20}$), and a linear or branched alkynyl ($C_2$-$C_{20}$), with the proviso that $R_1$ and $R_2$ are not both selected from H and D. In certain non-limiting embodiments, the amino acid side chain is not derived from an aromatic amino acid such as phenylalanine, such that in certain embodiments at least one of $R_1$ and $R_2$ is not aromatic.

In particular, non-limiting embodiments of Structural Formula I, the amino acid side chain compound may be selected from the group consisting of side chains of glycine, alanine, valine, isoleucine, leucine, and persephanine. Alternatively and/or in addition thereto, the linear or branched alkyl may selected from the group consisting of ethyl, n-propyl, n-butyl, and an alkyl comprising from 5 to 20 carbons. Alternatively and/or in addition thereto, at least one of $R_1$ and $R_2$ may be a branched alkyl comprising from 5 to 20 carbons. Alternatively and/or in addition thereto, one of $R_1$ and $R_2$ may be a branched alkyl comprising 11 carbons, and the other of $R_1$ and $R_2$ is H. Alternatively and/or in addition thereto, the amino acid side chain of at least one of $R_1$ and $R_2$ may be a persephanine side chain. Alternatively and/or in addition thereto, at least one of $R_1$ and $R_2$ may be an alkenyl. Alternatively and/or in addition thereto, at least one of $R_1$ and $R_2$ may be an alkynyl.

In a particular (but non-limiting) embodiment, the compound of Structural Formula I may comprise the structure:

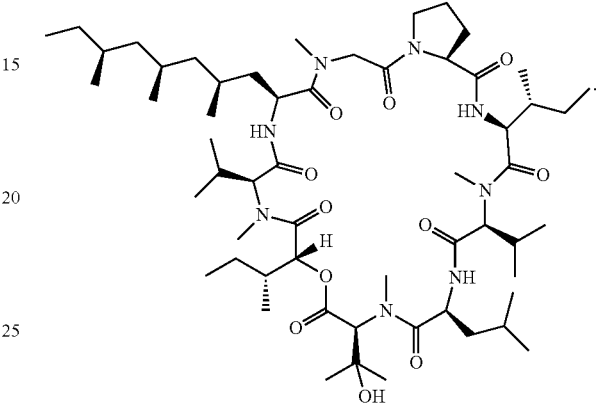

In certain non-limiting embodiments, the present disclosure is directed to the class of compounds (active agents) represented by Structural Formula II and stereoisomers thereof:

II

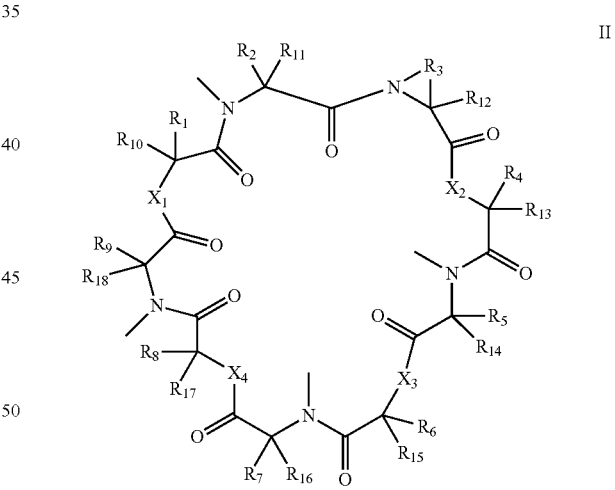

Wherein:

$X_1$ is selected from the group consisting of NH, O, N-methyl, and $CH_2$;

$X_2$ is selected from the group consisting of NH, O, N-methyl, and $CH_2$;

$X_3$ is selected from the group consisting of NH, O, N-methyl, and $CH_2$;

$X_4$ is selected from the group consisting of O, NH, N-methyl, and $CH_2$;

$R_1$ is selected from the group consisting of a persephanine side chain and structural and optical isomers thereof, straight chain or branched alkyl ($C_5$-$C_{20}$), straight chain or branched alkenyl ($C_5$-$C_{20}$), straight chain or branched alkynyl ($C_5$-

$C_{20}$), straight chain or branched alkyl ($C_5$-$C_{20}$) halide, straight chain or branched alkenyl ($C_5$-$C_{20}$) halide, straight chain or branched alkynyl ($C_5$-$C_{20}$) halide, straight chain or branched alkyl ($C_5$-$C_{20}$) amine, straight chain or branched alkenyl ($C_5$-$C_{20}$) amine, straight chain or branched alkynyl ($C_5$-$C_{20}$) amine, straight chain or branched alkyl ($C_5$-$C_{20}$) alcohol, straight chain or branched alkenyl ($C_5$-$C_{20}$) alcohol, straight chain or branched alkynyl ($C_5$-$C_{20}$) alcohol, straight chain or branched alkyl ($C_5$-$C_{20}$) ether, straight chain or branched alkenyl ($C_5$-$C_{20}$) ether, straight chain or branched alkynyl ($C_5$-$C_{20}$) ether, straight chain or branched alkyl ($C_5$-$C_{20}$) thiol, straight chain or branched alkenyl ($C_5$-$C_{20}$) thiol, straight chain or branched alkynyl ($C_5$-$C_{20}$) thiol, straight chain or branched alkyl ($C_5$-$C_{20}$) sulfide, straight chain or branched alkenyl ($C_5$-$C_{20}$) sulfide, straight chain or branched alkynyl ($C_5$-$C_{20}$) sulfide, straight chain or branched alkyl ($C_5$-$C_{20}$) sulfoxide, straight chain or branched alkenyl ($C_5$-$C_{20}$) sulfoxide, straight chain or branched alkynyl ($C_5$-$C_{20}$) sulfoxide, straight chain or branched alkyl ($C_5$-$C_{20}$) sulfone, straight chain or branched alkenyl ($C_5$-$C_{20}$) sulfone, straight chain or branched alkynyl ($C_5$-$C_{20}$) sulfone, straight chain or branched alkyl ($C_5$-$C_{20}$) nitrile, straight chain or branched alkenyl ($C_5$-$C_{20}$) nitrile, straight chain or branched alkynyl ($C_5$-$C_{20}$) nitrile, straight chain or branched alkyl ($C_5$-$C_{20}$) isonitrile, straight chain or branched alkenyl ($C_5$-$C_{20}$) isonitrile, straight chain or branched alkynyl ($C_5$-$C_{20}$) isonitrile, straight chain or branched alkyl ($C_5$-$C_{20}$) nitrite, straight chain or branched alkenyl ($C_5$-$C_{20}$) nitrite, straight chain or branched alkynyl ($C_5$-$C_{20}$) nitrite, straight chain or branched alkyl ($C_5$-$C_{20}$) oxime, straight chain or branched alkenyl ($C_5$-$C_{20}$) oxime, straight chain or branched alkynyl ($C_5$-$C_{20}$) oxime, straight chain or branched alkyl ($C_5$-$C_{20}$) nitroso, straight chain or branched alkenyl ($C_5$-$C_{20}$) nitroso, straight chain or branched alkynyl ($C_5$-$C_{20}$) nitroso, straight chain or branched alkyl ($C_5$-$C_{20}$) nitro, straight chain or branched alkenyl ($C_5$-$C_{20}$) nitro, straight chain or branched alkynyl ($C_5$-$C_{20}$) nitro, straight chain or branched alkyl ($C_5$-$C_{20}$) nitrate, straight chain or branched alkenyl ($C_5$-$C_{20}$) nitrate, straight chain or branched alkynyl ($C_5$-$C_{20}$) nitrate, straight chain or branched alkyl ($C_5$-$C_{20}$) imide, straight chain or branched alkenyl ($C_5$-$C_{20}$) imide, straight chain or branched alkynyl ($C_5$-$C_{20}$) imide, straight chain or branched alkyl ($C_5$-$C_{20}$) imine, straight chain or branched alkenyl ($C_5$-$C_{20}$) imine, straight chain or branched alkynyl ($C_5$-$C_{20}$) imine, straight chain or branched alkyl ($C_5$-$C_{20}$) amide, straight chain or branched alkenyl ($C_5$-$C_{20}$) amide, straight chain or branched alkynyl ($C_5$-$C_{20}$) amide, straight chain or branched alkyl ($C_5$-$C_{20}$) ester, straight chain or branched alkenyl ($C_5$-$C_{20}$) ester, straight chain or branched alkynyl ($C_5$-$C_{20}$) ester, straight chain or branched alkyl ($C_5$-$C_{20}$) ketone, straight chain or branched alkenyl ($C_5$-$C_{20}$) ketone, straight chain or branched alkynyl ($C_5$-$C_{20}$) ketone, straight chain or branched alkyl ($C_5$-$C_{20}$) carbonate, straight chain or branched alkenyl ($C_5$-$C_{20}$) carbonate, straight chain or branched alkynyl ($C_5$-$C_{20}$) carbonate, straight chain or branched (cyclopropyl)alkyl ($C_5$-$C_{20}$), straight chain or branched (cyclopropyl)alkenyl ($C_5$-$C_{20}$), straight chain or branched (cyclopropyl)alkynyl ($C_5$-$C_{20}$), straight chain or branched (cyclobutyl)alkyl ($C_5$-$C_{20}$), straight chain or branched (cyclobutyl)alkenyl ($C_5$-$C_{20}$), straight chain or branched (cyclobutyl)alkynyl ($C_5$-$C_{20}$), straight chain or branched alkyl ($C_5$-$C_{20}$) silane, straight chain or branched alkenyl ($C_5$-$C_{20}$) silane, straight chain or branched alkynyl ($C_5$-$C_{20}$) silane, straight chain or branched alkyl-$d_{1-10}$ ($C_5$-$C_{20}$), straight chain or branched alkenyl-$d_{1-10}$ ($C_5$-$C_{20}$), and straight chain or branched alkynyl-$d_{1-10}$ ($C_5$-$C_{20}$);

$R_2$ is selected from the group consisting of hydrogen (H), deuterium (D), methyl, ethyl, linear or branched alkyl ($C_3$-$C_{20}$), an amino acid side chain, a linear or branched alkenyl ($C_2$-$C_{20}$), and a linear or branched alkynyl ($C_2$-$C_{20}$);

$R_3$ is selected from the group consisting of alkyl or branched alkyl ($C_1$-$C_6$), alkyl ($C_1$-$C_6$) ether, and alkyl ($C_1$-$C_6$) amine;

$R_4$, $R_5$, $R_6$, $R_8$, $R_9$ are independently selected from the group consisting of straight chain or branched alkyl ($C_1$-$C_5$), straight chain or branched alkenyl ($C_1$-$C_5$), straight chain or branched alkynyl ($C_1$-$C_5$), straight chain or branched alkyl ($C_1$-$C_5$) halide, straight chain or branched alkenyl ($C_1$-$C_5$) halide, straight chain or branched alkynyl ($C_1$-$C_5$) halide, straight chain or branched alkyl ($C_1$-$C_5$) amine, straight chain or branched alkenyl ($C_1$-$C_5$) amine, straight chain or branched alkynyl ($C_1$-$C_5$) amine, straight chain or branched alkyl ($C_1$-$C_5$) alcohol, straight chain or branched alkenyl ($C_1$-$C_5$) alcohol, straight chain or branched alkynyl ($C_1$-$C_5$) alcohol, straight chain or branched alkyl ($C_1$-$C_5$) ether, straight chain or branched alkenyl ($C_1$-$C_5$) ether, straight chain or branched alkynyl ($C_1$-$C_5$) ether, straight chain or branched alkyl ($C_1$-$C_5$) thiol, straight chain or branched alkenyl ($C_1$-$C_5$) thiol, straight chain or branched alkynyl (($C_1$-$C_5$) thiol, straight chain or branched alkyl ($C_1$-$C_5$) sulfide, straight chain or branched alkenyl ($C_1$-$C_5$) sulfide, straight chain or branched alkynyl ($C_1$-$C_5$) sulfide, straight chain or branched alkyl ($C_1$-$C_5$) sulfoxide, straight chain or branched alkenyl ($C_1$-$C_5$) sulfoxide, straight chain or branched alkynyl ($C_1$-$C_5$) sulfoxide, straight chain or branched alkyl ($C_1$-$C_5$) sulfone, straight chain or branched alkenyl ($C_1$-$C_5$) sulfone, straight chain or branched alkynyl ($C_1$-$C_5$) sulfone, straight chain or branched alkyl ($C_1$-$C_5$) nitrile, straight chain or branched alkenyl ($C_1$-$C_5$) nitrile, straight chain or branched alkynyl ($C_1$-$C_5$) nitrile, straight chain or branched alkyl ($C_1$-$C_5$) isonitrile, straight chain or branched alkenyl ($C_1$-$C_5$) isonitrile, straight chain or branched alkynyl ($C_1$-$C_5$) isonitrile, straight chain or branched alkyl ($C_1$-$C_5$) nitrite, straight chain or branched alkenyl ($C_1$-$C_5$) nitrite, straight chain or branched alkynyl ($C_1$-$C_5$) nitrite, straight chain or branched alkyl ($C_1$-$C_5$) oxime, straight chain or branched alkenyl ($C_1$-$C_5$) oxime, straight chain or branched alkynyl ($C_1$-$C_5$) oxime, straight chain or branched alkyl ($C_1$-$C_5$) nitroso, straight chain or branched alkenyl ($C_1$-$C_5$) nitroso, straight chain or branched alkynyl ($C_1$-$C_5$) nitroso, straight chain or branched alkyl ($C_1$-$C_5$) nitro, straight chain or branched alkenyl ($C_1$-$C_5$) nitro, straight chain or branched alkynyl ($C_1$-$C_5$) nitro, straight chain or branched alkyl ($C_1$-$C_5$) nitrate, straight chain or branched alkenyl ($C_1$-$C_5$) nitrate, straight chain or branched alkynyl ($C_1$-$C_5$) nitrate, straight chain or branched alkyl ($C_1$-$C_5$) imide, straight chain or branched alkenyl ($C_1$-$C_5$) imide, straight chain or branched alkynyl ($C_1$-$C_5$) imide, straight chain or branched alkyl ($C_1$-$C_5$) imine, straight chain or branched alkenyl ($C_1$-$C_5$) imine, straight chain or branched alkynyl ($C_1$-$C_5$) imine, straight chain or branched alkyl ($C_1$-$C_5$) amide, straight chain or branched alkenyl ($C_1$-$C_5$) amide, straight chain or branched alkynyl ($C_1$-$C_5$) amide, straight chain or branched alkyl ($C_1$-$C_5$) ester, straight chain or branched alkenyl ($C_1$-$C_5$) ester, straight chain or branched alkynyl ($C_1$-$C_5$) ester, straight chain or branched alkyl ($C_1$-$C_5$) ketone, straight chain or branched alkenyl ($C_1$-$C_5$) ketone, straight chain or branched alkynyl ($C_1$-$C_5$) ketone, straight chain or branched alkyl ($C_1$-$C_5$) carbonate, straight chain or branched alkenyl ($C_1$-$C_5$) carbonate, straight chain or branched alkynyl ($C_1$-$C_5$) carbonate, straight chain or branched (cyclopropyl)alkyl ($C_1$-$C_5$) straight chain or branched (cyclopropyl)alkenyl ($C_1$-$C_5$), straight chain or branched (cyclopropyl)alkynyl ($C_1$-$C_5$), straight chain or branched (cyclobutyl)alkyl ($C_1$-$C_5$), straight chain or branched (cyclobutyl)alkenyl ($C_1$-$C_5$), straight chain or branched (cyclobutyl)alkynyl ($C_1$-$C_5$), straight chain or branched alkyl ($C_1$-$C_5$) silane, straight chain or branched alkenyl ($C_1$-$C_5$) silane, straight chain or branched alkynyl ($C_1$-$C_5$) silane, straight chain or branched alkyl-$d_{1-10}$ ($C_1$-$C_5$), straight chain or branched alkenyl-$d_{1-9}$ ($C_1$-$C_5$), straight chain or branched alkynyl-$d_{1-7}$ ($C_1$-$C_5$), methyl, ethyl, propyl, butyl, methyl imidazole, butyl amine, propyl guanidine, methyl-1-ol, ethyl-2-ol, ethyl-1-ol, ethyloic acid, propanoic acid, carboxymethyl, carboxyethyl, ethylamide, propylamide, methyl-1-thiol, ethyl-1-thiol, methyl sulfane, ethyl sulfane, isobutyl, sec-butyl, tert-butyl, and isopropyl;

$R_7$ is selected from the group consisting of straight chain or branched alkyl ($C_1$-$C_5$) alcohol, straight chain or branched alkenyl ($C_1$-$C_5$) alcohol, straight chain or branched alkynyl ($C_1$-$C_5$) alcohol, straight chain or branched alkyl ($C_1$-$C_5$) amine, straight chain or branched alkenyl ($C_1$-$C_5$) amine, straight chain or branched alkynyl ($C_1$-$C_5$) amine, straight chain or branched alkyl ($C_1$-$C_5$) thiol, straight chain or branched alkenyl ($C_1$-$C_5$) thiol, and straight chain or branched alkynyl ($C_1$-$C_5$) thiol; and $R_{10}$, $R_{11}$, $R_{12}$, $R_{13}$, $R_{14}$, $R_{15}$, $R_{16}$, $R_{17}$, and $R_{18}$ are independently selected from the group consisting of H, D, methyl, and ethyl, linear or branched alkyl ($C_3$-$C_5$).

In a particular (but non-limiting) embodiment, the compound of Structural Formula II may comprise the structure:

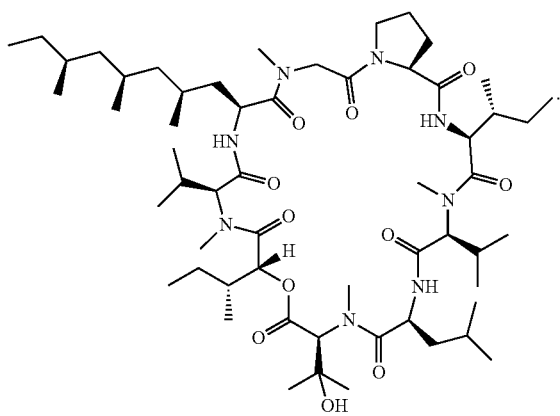 [SMILES: CC[C@H](C)C[C@H](C)C[C@H](C)C[C@@H]1NC(=O)[C@H](C(C)C)N(C)C(=O)[C@@H]([C@H](C)CC)OC(=O)[C@H](C(C)(C)O)N(C)C(=O)[C@H](CC(C)C)NC(=O)[C@H](C(C)C)N(C)C(=O)[C@H]([C@H](C)CC)NC(=O)[C@@H]2CCCN2C(=O)CN(C)C1=O]

In certain embodiments, the present disclosure is directed to the class of compounds (active agents) represented by Structural Formula III:

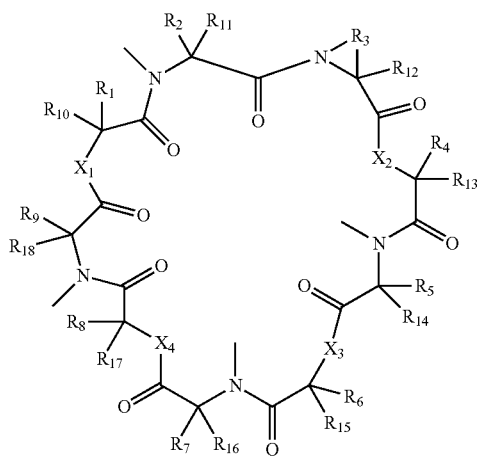

III wherein:

$X_1$ is selected from the group consisting of NH, O, N-methyl, and $CH_2$;

$X_2$ is selected from the group consisting of NH, O, N-methyl, and $CH_2$;

$X_3$ is selected from the group consisting of NH, O, N-methyl, and $CH_2$;

$X_4$ is selected from the group consisting of O, NH, N-methyl, and $CH_2$;

$R_1$ is selected from the group consisting of hydrogen (H), deuterium (D), methyl, ethyl, linear or branched alkyl ($C_3$-$C_{20}$), an amino acid side chain, a linear or branched alkenyl ($C_2$-$C_{20}$), and a linear or branched alkynyl ($C_2$-$C_{20}$);

$R_2$ is selected from the group consisting of a persephanine side chain and structural and optical isomers thereof, straight chain or branched alkyl ($C_5$-$C_{20}$), straight chain or branched alkenyl ($C_5$-$C_{20}$), straight chain or branched alkynyl ($C_5$-$C_{20}$), straight chain or branched alkyl ($C_5$-$C_{20}$) halide, straight chain or branched alkenyl ($C_5$-$C_{20}$) halide, straight chain or branched alkynyl ($C_5$-$C_{20}$) halide, straight chain or branched alkyl ($C_5$-$C_{20}$) amine, straight chain or branched alkenyl ($C_5$-$C_{20}$) amine, straight chain or branched alkynyl ($C_5$-$C_{20}$) amine, straight chain or branched alkyl ($C_5$-$C_{20}$) alcohol, straight chain or branched alkenyl ($C_5$-$C_{20}$) alcohol, straight chain or branched alkynyl ($C_5$-$C_{20}$) alcohol, straight chain or branched alkyl ($C_5$-$C_{20}$) ether, straight chain or branched alkenyl ($C_5$-$C_{20}$) ether, straight chain or branched alkynyl ($C_5$-$C_{20}$) ether, straight chain or branched alkyl ($C_5$-$C_{20}$) thiol, straight chain or branched alkenyl ($C_5$-$C_{20}$) thiol, straight chain or branched alkynyl ($C_5$-$C_{20}$) thiol, straight chain or branched alkyl ($C_5$-$C_{20}$) sulfide, straight chain or branched alkenyl ($C_5$-$C_{20}$) sulfide, straight chain or branched alkynyl ($C_5$-$C_{20}$) sulfide, straight chain or branched alkyl ($C_5$-$C_{20}$) sulfoxide, straight chain or branched alkenyl ($C_5$-$C_{20}$) sulfoxide, straight chain or branched alkynyl ($C_5$-$C_{20}$) sulfoxide, straight chain or branched alkyl ($C_5$-$C_{20}$) sulfone, straight chain or branched alkenyl ($C_5$-$C_{20}$) sulfone, straight chain or branched alkynyl ($C_5$-$C_{20}$) sulfone, straight chain or branched alkyl ($C_5$-$C_{20}$) nitrile, straight chain or branched alkenyl ($C_5$-$C_{20}$) nitrile, straight chain or branched alkynyl ($C_5$-$C_{20}$) nitrile, straight chain or branched alkyl ($C_5$-$C_{20}$) isonitrile, straight chain or branched alkenyl ($C_5$-$C_{20}$) isonitrile, straight chain or branched alkynyl ($C_5$-$C_{20}$) isonitrile, straight chain or branched alkyl ($C_5$-$C_{20}$) nitrite, straight chain or branched alkenyl ($C_5$-$C_{20}$) nitrite, straight chain or branched alkynyl ($C_5$-$C_{20}$) nitrite, straight chain or branched alkyl ($C_5$-$C_{20}$) oxime, straight chain or branched alkenyl ($C_5$-$C_{20}$) oxime, straight chain or branched alkynyl ($C_5$-$C_{20}$) oxime, straight chain or branched alkyl ($C_5$-$C_{20}$) nitroso, straight chain or branched alkenyl ($C_5$-$C_{20}$) nitroso, straight chain or branched alkynyl ($C_5$-$C_{20}$) nitroso, straight chain or branched alkyl ($C_5$-$C_{20}$) nitro, straight chain or branched alkenyl ($C_5$-$C_{20}$) nitro, straight chain or branched alkynyl ($C_5$-$C_{20}$) nitro, straight chain or branched alkyl ($C_5$-$C_{20}$) nitrate, straight chain or branched alkenyl ($C_5$-$C_{20}$) nitrate, straight chain or branched alkynyl ($C_5$-$C_{20}$) nitrate, straight chain or branched alkyl ($C_5$-$C_{20}$) imide, straight chain or branched alkenyl ($C_5$-$C_{20}$) imide, straight chain or branched alkynyl ($C_5$-$C_{20}$) imide, straight chain or branched alkyl ($C_5$-$C_{20}$) imine, straight chain or branched alkenyl ($C_5$-$C_{20}$) imine, straight chain or branched alkynyl ($C_5$-$C_{20}$) imine, straight chain or branched alkyl ($C_5$-$C_{20}$) amide, straight chain or branched alkenyl ($C_5$-$C_{20}$) amide, straight chain or branched alkynyl ($C_5$-$C_{20}$) amide, straight chain or branched alkyl ($C_5$-$C_{20}$) ester, straight chain or branched alkenyl ($C_5$-$C_{20}$) ester, straight chain or branched alkynyl ($C_5$-$C_{20}$)

ester, straight chain or branched alkyl ($C_5$-$C_{20}$) ketone, straight chain or branched alkenyl ($C_5$-$C_{20}$) ketone, straight chain or branched alkynyl ($C_5$-$C_{20}$) ketone, straight chain or branched alkyl ($C_5$-$C_{20}$) carbonate, straight chain or branched alkenyl ($C_5$-$C_{20}$) carbonate, straight chain or branched alkynyl ($C_5$-$C_{20}$) carbonate, straight chain or branched (cyclopropyl)alkyl ($C_5$-$C_{20}$), straight chain or branched (cyclopropyl)alkenyl ($C_5$-$C_{20}$), straight chain or branched (cyclopropyl)alkynyl ($C_5$-$C_{20}$), straight chain or branched (cyclobutyl)alkyl ($C_5$-$C_{20}$), straight chain or branched (cyclobutyl)alkenyl ($C_5$-$C_{20}$), straight chain or branched (cyclobutyl)alkynyl ($C_5$-$C_{20}$), straight chain or branched alkyl ($C_5$-$C_{20}$) silane, straight chain or branched alkenyl ($C_5$-$C_{20}$) silane, straight chain or branched alkynyl ($C_5$-$C_{20}$) silane, straight chain or branched alkyl-$d_{1-10}$ ($C_5$-$C_{20}$), straight chain or branched alkenyl-$d_{1-10}$ ($C_5$-$C_{20}$), and straight chain or branched alkynyl-$d_{1-10}$ ($C_5$-$C_{20}$);

$R_3$ is selected from the group consisting of alkyl or branched alkyl ($C_1$-$C_6$), alkyl ($C_1$-$C_6$) ether, and alkyl ($C_1$-$C_6$) amine;

$R_4$, $R_5$, $R_6$, $R_8$, $R_9$ are independently selected from the group consisting of straight chain or branched alkyl ($C_1$-$C_5$), straight chain or branched alkenyl ($C_1$-$C_5$), straight chain or branched alkynyl ($C_1$-$C_5$), straight chain or branched alkyl ($C_1$-$C_5$) halide, straight chain or branched alkenyl ($C_1$-$C_5$) halide, straight chain or branched alkynyl ($C_1$-$C_5$) halide, straight chain or branched alkyl ($C_1$-$C_5$) amine, straight chain or branched alkenyl ($C_1$-$C_5$) amine, straight chain or branched alkynyl ($C_1$-$C_5$) amine, straight chain or branched alkyl ($C_1$-$C_5$) alcohol, straight chain or branched alkenyl ($C_1$-$C_5$) alcohol, straight chain or branched alkynyl ($C_1$-$C_5$) alcohol, straight chain or branched alkyl ($C_1$-$C_5$) ether, straight chain or branched alkenyl ($C_1$-$C_5$) ether, straight chain or branched alkynyl ($C_1$-$C_5$) ether, straight chain or branched alkyl ($C_1$-$C_5$) thiol, straight chain or branched alkenyl ($C_1$-$C_5$) thiol, straight chain or branched alkynyl (($C_1$-$C_5$) thiol, straight chain or branched alkyl ($C_1$-$C_5$) sulfide, straight chain or branched alkenyl ($C_1$-$C_5$) sulfide, straight chain or branched alkynyl ($C_1$-$C_5$) sulfide, straight chain or branched alkyl ($C_1$-$C_5$) sulfoxide, straight chain or branched alkenyl ($C_1$-$C_5$) sulfoxide, straight chain or branched alkynyl ($C_1$-$C_5$) sulfoxide, straight chain or branched alkyl ($C_1$-$C_5$) sulfone, straight chain or branched alkenyl ($C_1$-$C_5$) sulfone, straight chain or branched alkynyl ($C_1$-$C_5$) sulfone, straight chain or branched alkyl ($C_1$-$C_5$) nitrile, straight chain or branched alkenyl ($C_1$-$C_5$) nitrile, straight chain or branched alkynyl ($C_1$-$C_5$) nitrile, straight chain or branched alkyl ($C_1$-$C_5$) isonitrile, straight chain or branched alkenyl ($C_1$-$C_5$) isonitrile, straight chain or branched alkynyl ($C_1$-$C_5$) isonitrile, straight chain or branched alkyl ($C_1$-$C_5$) nitrite, straight chain or branched alkenyl ($C_1$-$C_5$) nitrite, straight chain or branched alkynyl ($C_1$-$C_5$) nitrite, straight chain or branched alkyl ($C_1$-$C_5$) oxime, straight chain or branched alkenyl ($C_1$-$C_5$) oxime, straight chain or branched alkynyl ($C_1$-$C_5$) oxime, straight chain or branched alkyl ($C_1$-$C_5$) nitroso, straight chain or branched alkenyl ($C_1$-$C_5$) nitroso, straight chain or branched alkynyl ($C_1$-$C_5$) nitroso, straight chain or branched alkyl ($C_1$-$C_5$) nitro, straight chain or branched alkenyl ($C_1$-$C_5$) nitro, straight chain or branched alkynyl ($C_1$-$C_5$) nitro, straight chain or branched alkyl ($C_1$-$C_5$) nitrate, straight chain or branched alkenyl ($C_1$-$C_5$) nitrate, straight chain or branched alkynyl ($C_1$-$C_5$) nitrate, straight chain or branched alkyl ($C_1$-$C_5$) imide, straight chain or branched alkenyl ($C_1$-$C_5$) imide, straight chain or branched alkynyl ($C_1$-$C_5$) imide, straight chain or branched alkyl ($C_1$-$C_5$) imine, straight chain or branched alkenyl ($C_1$-$C_5$) imine, straight chain or branched alkynyl ($C_1$-$C_5$) imine, straight chain or branched alkyl ($C_1$-$C_5$) amide, straight chain or branched alkenyl ($C_1$-$C_5$) amide, straight chain or branched alkynyl ($C_1$-$C_5$) amide, straight chain or branched alkyl ($C_1$-$C_5$) ester, straight chain or branched alkenyl ($C_1$-$C_5$) ester, straight chain or branched alkynyl ($C_1$-$C_5$) ester, straight chain or branched alkyl ($C_1$-$C_5$) ketone, straight chain or branched alkenyl ($C_1$-$C_5$) ketone, straight chain or branched alkynyl ($C_1$-$C_5$) ketone, straight chain or branched alkyl ($C_1$-$C_5$) carbonate, straight chain or branched alkenyl ($C_1$-$C_5$) carbonate, straight chain or branched alkynyl ($C_1$-$C_5$) carbonate, straight chain or branched (cyclopropyl)alkyl ($C_1$-$C_5$) straight chain or branched (cyclopropyl)alkenyl ($C_1$-$C_5$), straight chain or branched (cyclopropyl)alkynyl ($C_1$-$C_5$), straight chain or branched (cyclobutyl)alkyl ($C_1$-$C_5$), straight chain or branched (cyclobutyl)alkenyl ($C_1$-$C_5$), straight chain or branched (cyclobutyl)alkynyl ($C_1$-$C_5$), straight chain or branched alkyl ($C_1$-$C_5$) silane, straight chain or branched alkenyl ($C_1$-$C_5$) silane, straight chain or branched alkynyl ($C_1$-$C_5$) silane, straight chain or branched alkyl-$d_{1-10}$ ($C_1$-$C_5$), straight chain or branched alkenyl-$d_{1-9}$ ($C_1$-$C_5$), straight chain or branched alkynyl-$d_{1-7}$ ($C_1$-$C_5$), methyl, ethyl, propyl, butyl, methyl imidazole, butyl amine, propyl guanidine, methyl-1-ol, ethyl-2-ol, ethyl-1-ol, ethyloic acid, propanoic acid, carboxymethyl, carboxyethyl, ethylamide, propylamide, methyl-1-thiol, ethyl-1-thiol, methyl sulfane, ethyl sulfane, isobutyl, sec-butyl, tert-butyl, and isopropyl;

$R_7$ is selected from the group consisting of straight chain or branched alkyl ($C_1$-$C_5$) alcohol, straight chain or branched alkenyl ($C_1$-$C_5$) alcohol, straight chain or branched alkynyl ($C_1$-$C_5$) alcohol, straight chain or branched alkyl ($C_1$-$C_5$) amine, straight chain or branched alkenyl ($C_1$-$C_5$) amine, straight chain or branched alkynyl ($C_1$-$C_5$) amine, straight chain or branched alkyl ($C_1$-$C_5$) thiol, straight chain or branched alkenyl ($C_1$-$C_5$) thiol, and straight chain or branched alkynyl ($C_1$-$C_5$) thiol; and $R_{10}$, $R_{11}$, $R_{12}$, $R_{13}$, $R_{14}$, $R_{15}$, $R_{16}$, $R_{17}$, and $R_{18}$ are independently selected from the group consisting of H, D, methyl, and ethyl, linear or branched alkyl ($C_3$-$C_5$).

In certain non-limiting embodiments, the present disclosure is directed to methods of treating a microbial infection in a subject in need of such treatment. The method comprises administering to the subject (human or non-human animal) an active agent comprising any of the compounds disclosed or otherwise contemplated herein, such as (but not limited to) a compound having a structure of any one of Structural Formulas I, II, or III or Compound I described herein. The microbial infection may be a fungal infection, protozoan infection, or bacterial infection. In a particular (but non-limiting) embodiment, the fungal infection may be an ocular fungal infection, and the compound is topically administered to an eye of the subject to be treated.

In certain non-limiting embodiments, the present disclosure is directed to methods of treating a fungal infection in a plant. The method comprises administering to the plant any of the compounds disclosed or otherwise contemplated herein, such as (but not limited to) a compound having a structure of any one of Structural Formulas I, II, or III or Compound I described herein.

In certain non-limiting embodiments, the present disclosure is directed to a composition comprising an active agent comprising any of the compounds disclosed or otherwise contemplated herein, such as (but not limited to) a compound having a structure of any one of Structural Formulas I, II, or III or Compound I described herein. In particular (but non-limiting) embodiments, the active agent may be present in the composition in combination with a secondary compound, such as described elsewhere herein.

In certain non-limiting embodiments, the present disclosure is directed to compounds for use in any of the methods described herein above (such as, but not limited to, methods of treating microbial infections in subjects as well as methods of treating fungal infections in plants). The compounds for use in this manner may be any of the compounds disclosed or otherwise contemplated herein, such as (but not limited to) a compound having a structure of any one of Structural Formulas I, II, or III or Compound I described herein.

The embodiments of the present disclosure also encompass processes, including methods of solid phase peptide synthesis and reactions in solution, that enable a person skilled in the art to produce cyclic peptides and depsipeptides, their salts, and intermediates in good yield and/or the required stereoisomerical purity. The monomer fragments can either be purchased or prepared using conventional chemistry or fermentation. For example, natural and synthetic α and β amino acids, e.g. Pro, Leu, Ile, Val, Ala, Arg, His, Lys, Asp, Glu, Ser, Thr, Phe, Asn, Gln, Cys, Trp, Tyr, Gly, Met, L-AIle (L-alloisoleucine), and D-HMP (D-2-hydroxy-3-methylpentanoic acid), are commercially available. N-methylated amino acids, e.g. N-Me-Gly, N-Me-Val, N-Me-Ile, N-Me-Leu, N-Me-Ala, and β-OH—N-Me-Val, can be obtained by methylation of N-protected (e.g. Fmoc and Boc) amino acid precursors using iodomethane or other methylating agents. The protecting groups can be removed from the prepared material using methods known to those skilled in the art. The α-hydroxy acids, e.g. HMP, can be converted from the corresponding α-amino acid analogs by diazotization-hydrolysis (e.g., see Muller et al., *ChemBioChem* (2009) 10:323-328). These methods and reagents are known to persons having ordinary skill in the art and would allow for the preparation of peptides and depsipeptides and their salts that are described in the examples and chemical formulas (e.g., Structural Formulas I, II, and III, and Compound 1) disclosed herein, as well as in the preparation of intermediates and their salts that would be used for the further manufacture or preparation of the peptides and depsipeptides and their salts that are described herein. These and related methods and reagents are described in the patent literature (for example, U.S. Pat. Nos. 9,493,512; 9,278,997; 9,067,978; 8,987,413; 8,614,289; 8,178,650; 6,316,406; 6,252,041; 6,001,815; and patents referenced therein) and are available to a person skilled in the art. These methods would allow for the manufacture of kilogram or multikilogram quantities of the disclosed peptides, depsipeptides, their salts, and intermediates.

The prepared or manufactured peptides, depsipeptides, their salts, and intermediates as disclosed herein may or may not require purification by chromatography using a sorbent (e.g., silica and reverse phase silica gels, optically active sorbents, resins) or solvent (e.g., partitioning, counter current separation, mixture of polyphasic solvents) or other chemical means (e.g., crystallization, recrystallization, salt formation, and precipitation) to achieve the final degree of purity. Purity of the manufactured products can include, but are not limited to, a range of acceptable parameters that include, but are not limited to: 40%-50.1%, 50%-60.1%, 60%-70.1%, 70%-80.1%, 80%-90.1%, or 90%-100%. In another embodiment, the purity of the peptides, depsipeptide, their salts, and intermediates can be specified as having a calculated percent purity between 40%-100% as measured by NMR, mass spectrometry, LCMS, HPLC, and other analytical means. The determination of the purity of the products from the preparation of the peptides, depsipeptides, their salts, and intermediates within these ranges of purity are known to and can be determined by a person skilled in the art.

The various $C_5$-$C_{20}$ chemical groups specified, for example, in $R_1$ and $R_2$ of Formula I, $R_1$ of Formula II, and $R_2$ of Formula III, including, but not limited to intermediates used in their preparation (e.g., amino acids, protected amino acids, esters, carboxylic acids, alkyl groups, alkenyl, alkynyl, and other compounds bearing a pendent $C_5$-$C_{20}$ chemical group) can be prepared synthetically or obtained from a natural source for the preparation of antifungal peptides, depsipetides, and their intermediates. In one non-limiting embodiment, the chemical group consisting of amino acids and protected amino acids can be prepared from their corresponding aldehyde analogs or any analogs (e.g., acids, hydroxyls, nitriles, alkenes, and alkynes) that can be converted into aldehydes conventionally. The aldehyde analogs can then be transformed into the desired amino acids following the methods as described in Machauer et al. (*Bioorg Med Chem Lett*. (2009) Mar. 1; 19(5):1366-70). In particular, an amino acid (e.g., persephanine including its structural (e.g., constitutional) and optical (e.g., configurational, including geometric, diastereomeric, and enantiomeric) isomers) comprising a reduced polypropylene side chain converted from its corresponding hydroxyl analog can be constructed via catalytic methods (e.g., Zr-catalyzed asymmetric C—C bond formation) with propylene precursors (e.g., as described in Negishi et al., *Proc Natl Acad Sci USA*. (2004) Apr. 20; 101(16):5782-7; and Ota et al., *Proc Natl Acad Sci USA*. (2016) Mar. 15; 113(11):2857-61). The monomer fragments can be subsequently assembled by Fmoc-solid-phase peptide synthesis (Fmoc-SPPS) to form a linear peptide (e.g., as shown in Kaur et al., *Org Lett*. (2015) Feb. 6; 17(3):492-5) or by other peptide and depsipeptide preparation methods that are known to one skilled in the art and described in the patent literature (for example, U.S. Pat. Nos. 9,493,512; 9,278,997; 9,067,978; 8,987,413; 8,614,289; 8,178,650; 6,316,406; 6,252,041; 6,001,815; and patents referenced therein). Combinations of coupling agents (e.g. EDC/NHS, EDC/HOBt, EDC/Pfp, DCC/HOBt, BTC, EEDQ, COCl2, FDP, FDDP, PyBOP, BOP, BOP/HOBt, HBTU) can be utilized for linking the α-N-protected and α-O-protected residues. The preparation of the antimicrobial peptide, depsipeptide, and its intermediates can involve the execution of a macrolactamization or macrolactonization reaction between the deprotected C-terminal and N-terminal residues, especially at those locations and atoms represented by X in Formulas II and Formula III.

In at least certain non-limiting embodiments, the active agents of the present disclosure may be combined with one or more secondary compounds, such as (but not limited to) a pharmaceutically acceptable component (e.g., a carrier, vehicle, excipient, and/or diluent), to form a pharmaceutical composition for use in accordance with the methods of the present disclosure, for example (but not by way of limitation) for treating fungal infections. Such a composition may contain, in addition to the active agent and carrier, diluents, fillers, salts, buffers, stabilizers, solubilizers, and other materials well known in the art. Suitable carriers, vehicles and other components of the formulation are described, for example, in *Remington: The Science and Practice of Pharmacy*, $22^{nd}$ ed.

Where used herein, the term "secondary compound" refers to any compound used in combination (e.g., in a composition or formulation) with an anti-microbial active agent of the present disclosure (such as, but not limited to, the primary compound having a structure as defined in Structural Formula I, II, or III or Compound I), for example, for aiding in delivery of the active agent to the subject or organism to be treated. The term "pharmaceutically acceptable" means a non-toxic material that does not interfere with the effectiveness of the biological activity of the active agent. The characteristics of the carrier will depend on the route of administration.

For example, but not by way of limitation, the active agent may be dissolved in a secondary compound such as a physiologically acceptable pharmaceutical carrier, vehicle, excipient, or diluent and administered as either a solution or a suspension. Non-limiting examples of suitable pharmaceutically acceptable carriers include water, saline, dextrose solutions, fructose solutions, ethanol, or oils of animal, vegetative, or synthetic origin, or any combination thereof. A sterile diluent, which may contain materials generally recognized for approximating physiological conditions and/or as required by governmental regulations, may be employed as the pharmaceutically acceptable carrier. In this respect, the sterile diluent may contain a buffering agent to obtain a physiologically acceptable pH, such as (but not limited to) sodium chloride, saline, phosphate-buffered saline, and/or other substances which are physiologically acceptable and/or safe for use.

The pharmaceutical compositions may also contain one or more additional components in addition to the active agent and pharmaceutically acceptable carrier(s) (and other additional therapeutically active agent(s), if present). Examples of secondary compounds that may be present include, but are not limited to, diluents, fillers, salts, buffers, preservatives, stabilizers, solubilizers, and other materials well known in the art. Another particular non-limiting example of an additional component that may be present in the pharmaceutical composition is a delivery agent, as discussed in further detail herein below.

Some examples of suitable excipients or carriers include (but are not limited to): lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as (but not limited to) talc, magnesium stearate, and mineral oil; wetting agents; emulsifying and suspending agents; preserving agents such as (but not limited to) methyl- and propylhydroxy-benzoates; sweetening agents; and flavoring agents. The compositions can be formulated so as to provide quick, sustained, or delayed release of the active agent after administration to the patient by employing procedures known in the art.

For preparing solid compositions such as (but not limited to) tablets or other solid dosage forms, the principal active agent can be mixed with a pharmaceutical excipient or carrier to form a solid preformulation composition containing a homogeneous mixture of the active agent. When referring to these preformulation compositions as homogeneous, it is meant that the active agent is dispersed evenly throughout the composition so that the composition may be readily subdivided into equally effective unit dosage forms such as tablets, pills, and capsules. In another embodiment, the active agent(s) of the present disclosure can be tableted with conventional tablet bases such as (but not limited to) lactose, sucrose, and cornstarch in combination with binders, such as (but not limited to) acacia, cornstarch, or gelatin, disintegrating agents such as (but not limited to) potato starch or alginic acid, and a lubricant such as (but not limited to) stearic acid or magnesium stearate.

The dosage forms may be coated or otherwise compounded to provide a dosage form affording the advantage of prolonged action. For example, the tablet or pill can comprise an inner dosage component and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate. Similarly, when administered orally, the present compositions may be protected from digestion. This can be accomplished either by complexing the active agent with a composition to render it resistant to acidic and enzymatic hydrolysis or by packaging active agent in an appropriately resistant carrier such as a liposome, e.g., such as shown in U.S. Pat. No. 5,391,377.

The liquid forms in which the novel compositions of the present disclosure may be incorporated for administration orally or by injection include (but are not limited to) aqueous solutions, suitably flavored syrups, aqueous or oil suspensions, and flavored emulsions with edible oils such as (but not limited to) corn oil, cottonseed oil, sesame oil, coconut oil, or peanut oil, as well as elixirs and similar pharmaceutical vehicles. In some embodiments, the active agent is administered in solution. The formulation thereof may be in a solution having a suitable pharmaceutically acceptable buffer such as (but not limited to) phosphate, Tris (hydroxymethyl) aminomethane-HCl or citrate, and the like. Buffer concentrations should be in the range of 1 to 100 mM. The formulated solution may also contain a salt, such as (but not limited to) sodium chloride or potassium chloride, in a concentration of 50 to 150 mM. An effective amount of a stabilizing agent such as (but not limited to) mannitol, trehalose, sorbitol, glycerol, albumin, a globulin, a detergent, a gelatin, a protamine, or a salt of protamine may also be included.

Other non-limiting embodiments of the pharmaceutical compositions of the present disclosure may include the incorporation or entrapment of the active agent in various types of drug delivery systems (secondary compounds) that function to provide targeted delivery, controlled release, and/or increased half-life to the active agent. For example, but not by way of limitation, it is possible to entrap the active agent in microcapsules prepared by coacervation techniques or by interfacial polymerization (for example, hydroxymethylcellulose or gelatin-microcapsules and poly-(methylmethacylate) microcapsules, respectively). It is also possible to entrap the active agent in macroemulsions or colloidal drug delivery systems (such as, but not limited to, liposomes, albumin microspheres, microemulsions, nanoparticles, nanocapsules, and the like). Such techniques are well known to persons having ordinary skill in the art, and thus no further description thereof is deemed necessary.

Active agents and compositions of the present disclosure may be administered via one or more routes of administration using one or more of a variety of methods known in the art. As will be appreciated by the skilled artisan, the route and/or mode of administration will vary depending upon the desired results. Selected routes of administration include (but are not limited to) intravenous, intramuscular, intradermal, intraperitoneal, subcutaneous, spinal, or other parenteral routes of administration, for example by injection or infusion. The active agent can be delivered alone or as pharmaceutical compositions by any means known in the art, e.g., systemically, regionally, or locally; by intra-arterial, intrathecal (IT), intravenous (IV), parenteral, intra-pleural cavity, topical, oral, or local administration, as subcutaneous, intra-tracheal (e.g., by aerosol), or transmucosal (e.g., buccal, bladder, vaginal, uterine, rectal, nasal mucosa). Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, and intrasternal injection and infusion. Alternatively, compositions can be administered via a non-parenteral route, such as a topical, epidermal, or mucosal route of administration, for example, intranasally, orally, vaginally, rectally, sublingually, or topically. In one embodiment, the composition is administered by infusion. In another embodiment, the composition is administered subcutaneously. In another embodiment, the composition is administered orally. In another embodiment, the composition is administered to the ear canal. In another embodiment, the composition is administered transdermally. In another embodiment, the composition is administered to the lungs with no penetration, partial penetration, or complete penetration of the lung tissues. In another embodiment, the composition is administered to the surface of the skin with no penetration, partial penetration, or complete penetration of the epidermis. In another embodiment, the composition is administered to the surface of the skin with no penetration, partial penetration, or complete penetration of the dermis. In another embodiment, the composition is administered to the surface of the skin with no penetration, partial penetration, or complete penetration of the subcutaneous tissue (hypodermis). In another embodiment, the composition is administered to the surface or interior portion or portion of the eye. In another embodiment, the composition is administered to the eye with no penetration, partial penetration, or complete penetration of the cornea. In another embodiment, the composition is administered to the eye with no penetration, partial penetration, or complete penetration of the anterior chamber. In another embodiment, the composition is administered to the eye with no penetration, partial penetration, or complete penetration of the posterior chamber. In another embodiment, the composition is administered to the eye with no penetration, partial penetration, or complete penetration of the vitreous humor.

Compositions for inhalation or insufflation include solutions and suspensions in pharmaceutically acceptable, aqueous, or organic solvents, or mixtures thereof, and powders. The liquid or solid compositions may contain suitable pharmaceutically acceptable excipients as described supra.

The compositions can be administered by the oral or nasal respiratory route for local or systemic effect. Compositions in pharmaceutically acceptable solvents may be nebulized by use of inert gases. Nebulized solutions may be inhaled directly from the nebulizing device, or the nebulizing device may be attached to a face mask tent or intermittent positive pressure breathing machine. Solution, suspension, or powder compositions may also be administered orally or nasally from devices which deliver the formulation in an appropriate manner.

As noted, the active agent can be combined with a pharmaceutically acceptable carrier (excipient) or vehicle to form a pharmacological composition. Pharmaceutically acceptable carriers can contain a physiologically acceptable compound that acts to stabilize, increase, or decrease the absorption or clearance rates of the pharmaceutical compositions. Physiologically acceptable carriers and vehicles can include, for example (but not by way of limitation), carbohydrates, such as glucose, sucrose, or dextrans; antioxidants, such as ascorbic acid or glutathione; chelating agents; low molecular weight proteins; detergents; liposomal carriers; or excipients or other stabilizers and/or buffers. Other non-limiting examples of physiologically acceptable compounds, carriers, and vehicles include wetting agents, emulsifying agents, dispersing agents, or preservatives.

For transmucosal or transdermal administration, penetrants appropriate to the barrier to be permeated can be used in the formulation. Such penetrants (i.e., secondary compounds) are generally known in the art, and include, e.g., for transmucosal administration, bile salts and fusidic acid derivatives. In addition, detergents can be used to facilitate permeation. Transmucosal administration can be through nasal sprays or using suppositories. For topical, transdermal administration, the active agents are formulated into ointments, creams, salves, powders, and gels. Transdermal delivery systems can also include, e.g., patches. The present compositions can also be administered in sustained delivery or sustained release mechanisms. For example, biodegradeable microspheres or capsules or other biodegradeable polymer configurations capable of sustained delivery of the active agent can be included herein.

In one particular, non-limiting example, the secondary compound may include a liposome in which the active agent is disposed. In addition to other pharmaceutically acceptable carrier(s), the liposome may contain amphipathic agents such as lipids which exist in an aggregated form as micelles, insoluble monolayers, liquid crystals, or lamellar layers in aqueous solution. Suitable lipids for liposomal formulation include, but are not limited to, monoglycerides, diglycerides, amphipathic lipids, alkyl alcohols, sulfatides, lysolecithin, phospholipids, saponin, bile acids, combinations thereof, and the like. Preparation of such liposomal formulations is well within the level of ordinary skill in the art, as disclosed, for example, in U.S. Pat. Nos. 4,235,871; 4,501,728; 4,837,028; and 4,737,323. The active agents of the present disclosure can be administered in the form of a liposome. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior. The aqueous portion contains the active agent to be delivered. In order to cross intact mammalian skin, lipid vesicles must pass through a series of fine pores, each with a diameter less than 50 nm, under the influence of a suitable transdermal gradient. Therefore, it is desirable in certain embodiments to use a liposome which is highly deformable and able to pass through such fine pores. Liposomes can be made from phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example (but not by way of limitation), soybean PC, and egg PC. In one embodiment, the pharmaceutical formulations comprising the active agent are incorporated in lipid monolayers or bilayers, e.g., liposomes, such as shown in U.S. Pat. Nos. 6,110,490; 6,096,716; 5,283,185; and 5,279,833. Liposomes and liposomal formulations can be prepared according to standard methods and are also well known in the art, such as U.S. Pat. Nos. 4,235,871; 4,501,728; and 4,837,028.

In other non-limiting examples, the active agent of the present disclosure may be incorporated into particles of one or more polymeric secondary compounds, as this type of incorporation can be useful in controlling the duration of action of the active agent by allowing for controlled release from the preparations, thus increasing the half-life thereof. Non-limiting examples of polymeric materials that may be utilized in this manner include polyesters, polyamides, polyamino acids, hydrogels, poly(lactic acid), ethylene vinylacetate copolymers, copolymer micelles of, for example, PEG and poly(l-aspartamide), and combinations thereof.

Additional pharmaceutical methods may be employed to control the duration of action of the active agent(s). Increased half-life and controlled release preparations may be achieved through the use of polymers to conjugate, complex with, absorb, or contain the active agent(s) described herein. The controlled delivery and/or increased half-life may be achieved by selecting appropriate macromolecules (for example, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide, proteins (e. g., bovine serum albumin or human serum albumin) polyethylene glycol (PEG), poly(L-aspartamide) with an appropriate concentration of the active pharmaceutical in order to control release.

When the active agent(s) is to be used as an injectable material, it can be formulated into a conventional injectable carrier. Non-limiting examples of suitable carriers include biocompatible and pharmaceutically acceptable phosphate buffered saline solutions, which are particularly isotonic.

For reconstitution of a lyophilized product in accordance with the present disclosure, one may employ a sterile diluent, which may contain materials generally recognized for approximating physiological conditions and/or as required by governmental regulation. In this respect, the sterile diluent may contain a buffering agent to obtain a physiologically acceptable pH, such as (but not limited to) sodium chloride, saline, phosphate-buffered saline, and/or other substances which are physiologically acceptable and/or safe for use. In general, the material for intravenous injection in humans should conform to regulations established by the Food and Drug Administration, which are available to those in the field. The pharmaceutical composition may also be in the form of an aqueous solution containing many of the same substances as described above for the reconstitution of a lyophilized product.

The active agent(s) of the present disclosure can also be administered as a pharmaceutically acceptable acid- or base-addition salt, formed by reaction with inorganic acids such as (but not limited to) hydrochloric acid, hydrobromic acid, perchloric acid, nitric acid, thiocyanic acid, sulfuric acid, and phosphoric acid; and organic acids such as (but not limited to) formic acid, acetic acid, propionic acid, glycolic acid, lactic acid, pyruvic acid, oxalic acid, malonic acid, succinic acid, maleic acid, and fumaric acid; or by reaction with an inorganic base such as (but not limited to) sodium hydroxide, ammonium hydroxide, potassium hydroxide; and organic bases such as (but not limited to) mono-, di-, trialkyl and aryl amines and substituted ethanolamines.

As used herein, a pharmaceutically-acceptable carrier, vehicle, diluent, or excipient may also refer to a pharmaceutically-acceptable solvent, suspending agent, or material for delivering the active agent(s) of the present disclosure to the subject. In one non-limiting embodiment, an ophthalmically-acceptable vehicle, carrier, diluent, or excipient is an ophthalmically-acceptable solvent, suspending agent, or material for delivering the active agents of the present disclosure to an eye of the subject. The carrier may be liquid or solid and is selected with the planned manner of administration in mind. Examples of pharmaceutically-acceptable vehicles, carriers, diluents, or excipients, and/or ophthalmically-acceptable vehicles, carriers, diluents, or excipients that may be utilized in accordance with the present disclosure include, but are not limited to, polyethylene glycol (PEG), polyvinylpyrrolidine (PVP), polyvinyl alcohol (PVA), sodium hyaluronate, hydroxypropyl methylcellulose, carboxymethylcellulose, polymers, carboxymethylcellulose, cyclodextrins, liposomes, ethanol, DMSO, polyionic vehicles, polyionic vehicles, colloidal systems, ointments, aqueous buffers, gel-forming systems, saline solutions, solvents, oils, DPPC, lipids, and combinations thereof. Other examples include, but are not limited to, biocompatible hydrogels, bandages, inserts, and contact lenses, which can also be coated, infused, or filled with the active agent and placed directly on the eye. The pharmaceutical compositions described or otherwise contemplated herein may further comprise at least one delivery agent that assists in delivery of the active agents to a desired site of delivery; for example but not by way of limitation, at least one delivery agent may be included in an ophthalmic composition to assist in the penetration of a surface of an eye; in certain embodiments, the delivery agent may assist in delivery to any or all parts of the eye and its attendant tissues, muscles, nerves, and organs. For example, in order for a topical application to be effective, the composition may need to be able to penetrate the surface of the eye so that it can travel to the desired tissue. This may include penetrating the conjunctiva and/or the cornea.

For ophthalmic compositions, the active agent may be prepared in a solution referred to as "artificial tears" in order to mimic the physiological osmotic properties of human lacrimal secretions. These compositions may contain stabilizers, thickening agents, and buffers to preserve and/or enhance delivery of the active pharmaceutical ingredient, to achieve proper tonicity, to achieve a desirable viscosity, and/or to compliment the active pharmaceutical ingredient's action. These methods are known to those trained in the art and require no further elaboration.

For ophthalmic compositions, the active agent may be combined with preservatives to prevent microbial growth. Preservatives may include, but are not limited to, benzalkonium chloride (BAC or BAK), benzethonium chloride, chlorhexidine, mercurial compounds such as thimerosal, chlorobutanol, parabens, stabilized oxychloro-complex (PURITE®, Allergan, Inc.) and sodium perborate (oxidation), EDTA.

For ophthalmic compositions, the active agent may be combined with surfactants. The surfactant may be an amphiphilic chemical substance to aid or control delivery or to prevent or disrupt microbial growth.

The term "topical" as used herein to define a mode of administration, means that a material is administered by being applied to an epithelial surface or tissue. In addition, as noted, the compositions of the present disclosure may be designed to provide delayed, controlled, extended, and/or sustained release using formulation techniques which are well known in the art.

As used herein, the term "concurrent therapy" is used interchangeably with the terms "combination therapy" and "adjunct therapy," and will be understood to mean that the subject in need of treatment is treated or given another drug for the condition in conjunction with the pharmaceutical compositions of the present disclosure. This concurrent therapy can be sequential therapy, where the patient is treated first with one composition and then the other composition, or the two compositions are given simultaneously.

Another non-limiting embodiment of the present disclosure is directed to a kit that contains one or more of any of the active agents and/or pharmaceutical compositions described or otherwise contemplated herein. The kit may further contain a secondary compound as described herein above for use concurrently with the pharmaceutical composition(s). If the composition present in the kit is not provided in the form in which it is to be delivered, the kit may further contain a pharmaceutically acceptable carrier, vehicle, diluent, or other agent for mixing with the active agent for preparation of the pharmaceutical composition. The kit including the composition and/or other reagents may also be packaged with instructions packaged for administration and/or dosing of the compositions contained in the kit. The instructions may be fixed in any tangible medium, such as printed paper, or a computer-readable magnetic or optical medium, or instructions to reference a remote computer data source such as a worldwide web page accessible via the internet.

The kit may contain single or multiple doses of the pharmaceutical composition which contains the active agent. When multiple doses are present, the doses may be disposed in bulk within a single container, or the multiple doses may be disposed individually within the kit; that is, the pharmaceutical compositions may be present in the kit in unit dosage forms to facilitate accurate dosing. The term "unit dosage forms" as used herein refers to physically discrete units suitable as unitary dosages for human subjects and other mammals; each unit contains a predetermined quantity of the active agent calculated to produce the desired therapeutic effect, in association with a suitable pharmaceutical excipient. Typical unit dosage forms of liquid compositions include prefilled, premeasured ampules or syringes; for solid compositions, typical unit dosage forms include pills, tablets, capsules, or the like. In such compositions, the active agent may sometimes be a minor component (from about 0.1% to about 50% by weight, such as but not limited to, from about 1% to about 40% by weight) with the remainder being various vehicles or carriers and processing aids helpful for forming the desired dosing form.

The active agent may be provided as a "pharmaceutically acceptable salt," which refers to salts that retain the biological effectiveness and properties of a compound and which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly examples include (but are not limited to) the ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in international patent application Publication No. WO 87/05297, published Sep. 11, 1987 to Johnston et al.

The amount of the active agent that is effective in the treatment described herein can be determined by the attending diagnostician, as one of ordinary skill in the art, by the use of conventional techniques and by observing results obtained under analogous circumstances. In determining the therapeutically effective dose, a number of factors may be considered by the attending diagnostician, including, but not limited to: the species of the subject; its size, age, and general health; the specific diseases or other conditions involved; the degree, involvement, and/or severity of the diseases or conditions; the response of the individual subject; the particular active agent administered; the mode of administration; the bioavailability characteristics of the preparation administered; the dose regimen selected; the use of concomitant medication; and other relevant circumstances. A therapeutically effective amount of an active agent of the present disclosure also refers to an amount of the active agent which is effective in controlling, reducing, or ameliorating the condition to be treated or may refer to the amount of the active agent required to achieve a prophylactic effect for the purpose of preventing, controlling, reducing, or ameliorating the condition to be treated.

Practice of the method of the present disclosure may include administering to a subject a therapeutically effective amount of the pharmaceutical composition (containing the active agent in any suitable systemic and/or local formulation), in an amount effective to deliver the dosages listed above. The dosage can be administered, for example, but not by way of limitation, on a one-time basis, or administered at multiple times (for example, but not by way of limitation, from one to five times per day, or once or twice per week). The pharmaceutical composition may be administered either alone or in combination with other therapies, in accordance with the inventive concepts disclosed herein.

Compositions of the active agent can be administered in a single dose treatment or in multiple dose treatments on a schedule and over a time period appropriate to the age, weight, and condition of the subject, the particular composition used, and the route of administration. In one embodiment, a single dose of the composition according to the disclosure is administered. In other embodiments, multiple doses are administered. The frequency of administration can vary depending on any of a variety of factors, e.g., severity of the symptoms, degree of immunoprotection desired, or whether the composition is used for prophylactic or curative purposes. For example, in certain embodiments, the composition is administered once per day, twice per day, three times per day, every other day, once per week, twice per week, three times per week, four times per week, five times per week, six times per week, or seven times per week. The duration of treatment, e.g., the period of time over which the composition is administered, can vary, depending on any of a variety of factors, e.g., subject response. For example, the composition can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

The composition may comprise the active agent in a concentration of, but is not limited to, 0.0001 M to 1 M, for example, or 0.001 M to 0.1 M. The composition may comprise about 0.01 to about 1000 milligrams of the active agent (compound) per ml of at least one secondary compound with which the active agent is combined in a composition or mixture. The composition may comprise about 1 wt % to about 90 wt % (or 1 mass % to about 90 mass %) of one or more active agents and about 10 wt % to about 99 wt % (or 10 mass % to about 99 mass %) of one or more secondary compounds (where "wt %" is defined as the percentage by weight of a particular compound in a solid or liquid composition, and "mass %" is defined as the percentage by mass of a particular compound in a solid or liquid composition).

The active agents of the present disclosure may be present in the pharmaceutical compositions at any concentration that allows the pharmaceutical composition to function in accordance with the present disclosure; for example, but not by way of limitation, the compound(s) may be present in a range having a lower level selected from about 0.0001%, about 0.005%, about 0.001%, about 0.005%, about 0.01%, about 0.05%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, and about 2.0%; and an upper level selected from about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, and about 95%. Non-limiting examples of particular ranges include a range of from about 0.0001% to about 95%, a range of from about 0.001% to about 75%; a range of from about 0.005% to about 50%; a range of from about 0.01% to about 40%; a range of from about 0.05% to about 35%; a range of from about 0.1% to about 30%; a range of from about 0.1% to about 25%; a range of from about 0.1% to about 20%; a range of from about 1% to about 15%; a range of from about 2% to about 12%; a range of from about 5% to about 10%; and the like. Any other range that includes a lower level selected from the above-listed lower level concentrations and an upper level selected from the above-listed upper level concentrations also falls within the scope of the present disclosure.

For example, but not by way of limitation, the therapeutically effective amount of an active agent used in the present disclosure will generally contain sufficient active agent to deliver in a range of from about 0.01 µg/kg to about 10 mg/kg (weight of active agent/body weight of patient). For example, but not by way of limitation, the composition will deliver about 0.1 µg/kg to about 5 mg/kg, and more particularly about 1 µg/kg to about 1 mg/kg.

Exemplary, non-limiting ranges for a therapeutically or prophylactically effective amount of the active agent include but are not limited to about 0.001 mg/kg of the subject's body weight to about 100 mg/kg of the subject's body weight, more typically about 0.01 mg/kg to about 100 mg/kg, about 0.1 mg/kg to about 50 mg/kg, about 0.1 mg/kg to about 40 mg/kg, about 1 mg/kg to about 30 mg/kg, or about 1 mg/kg to about 20 mg/kg, or about 2 mg/kg to about 30 mg/kg, about 2 mg/kg to about 20 mg/kg, about 2 mg/kg to about 15 mg/kg, about 2 mg/kg to about 12 mg/kg, or about 2 mg/kg to about 10 mg/kg, or about 3 mg/kg to about 30 mg/kg, about 3 mg/kg to about 20 mg/kg, about 3 mg/kg to about 15 mg/kg, about 3 mg/kg to about 12 mg/kg, or about 3 mg/kg to about 10 mg/kg, or about 5 mg to about 1500 mg, as a fixed dosage.

The composition is formulated to contain an effective amount of the active agent, wherein the amount depends on the animal to be treated and the condition to be treated. In certain embodiments, the active agent is administered at a dose ranging from about 0.001 mg to about 10 g, from about 0.01 mg to about 10 g, from about 0.1 mg to about 10 g, from about 1 mg to about 10 g, from about 1 mg to about 9 g, from about 1 mg to about 8 g, from about 1 mg to about 7 g, from about 1 mg to about 6 g, from about 1 mg to about 5 g, from about 10 mg to about 10 g, from about 50 mg to about 5 g, from about 50 mg to about 5 g, from about 50 mg to about 2 g, from about 0.05 µg to about 1.5 mg, from about 10 µg to about 1 mg protein, from about 30 µg to about 500 µg, from about 0.1 µg to about 200 mg, from about 0.1 µg to about 5 µg, from about 5 µg to about 10 µg, from about 10 µg to about 25 µg, from about 25 µg to about 50 µg, from about 50 µg to about 100 µg, from about 100 µg to about 500 µg, from about 500 µg to about 1 mg, or from about 1 mg to about 2 mg. The specific dose level for any particular subject depends upon a variety of factors including the activity of the specific peptide, the age, body weight, general health, sex, diet, time of administration, route of administration, and rate of excretion, drug combination, and the severity of the particular disease undergoing therapy.

The dosage of an administered active agent for the subject will vary depending upon such factors as the patient's age, weight, height, sex, general medical condition, and previous medical history. In certain non-limiting embodiments, the recipient is provided with a dosage of the active agent that is in the range of from about 1 mg to about 1000 mg as a single infusion or single or multiple injections, although a lower or higher dosage also may be administered. The dosage may be in the range of from about 25 mg to about 100 mg of the active agent per square meter (m$^2$) of body surface area for a typical adult, although a lower or higher dosage also may be administered. Examples of dosages that may be administered to a human subject further include, for example, about 1 mg to about 500 mg, about 1 mg to about 70 mg, or about 1 mg to about 20 mg, although higher or lower doses may be used. Dosages may be repeated as needed, for example (but not by way of limitation), once per week for 4-10 weeks, or once per week for 8 weeks, or once per week for 4 weeks. It may also be given less frequently, such as every other week for several months, or more frequently, such as twice weekly, or by continuous infusion.

In alternative embodiments, the active agents described herein can be used in agricultural applications, for example in treatments of plants, algae, and animals including, but not limited to, the treatment, control, and prevention of fungal infections in plants of horticultural and agricultural use, biorenewable biomass, and chemical production, and farmed animals. The active ingredients may be used to control, treat, or prevent diseases caused by soil-born, air-born, water-born, or insect-born fungal disease-causing agents including established and emerging plant pathogens.

Agricultural applications include, but are not limited to, rice, cattle, pigs, chickens, poultry, wheat, soybeans, tomatoes, sugarcane, maize, potatoes, other vegetable, grapes, cotton, apples, bananas, cassava, mangos, sheep, coffee, palm oil, onion, beans, peanuts, olives, rapeseed, chilies, tea, oranges, rubber, cucumbers, yams, peaches, lettuce, cacao, goats, sunflowers, sugar beets, watermelons, buffalo, asparagus, turkey, carrots, duck, coconuts, tangerines, almonds, lemons, limes, strawberries, walnuts, lawn grass, commercial turf, and ornamental flowers and flowers used in floral designs (including, but not limited to, roses, carnations, tulips, daisies, sunflowers, daffodils, orchids, and other flowers known to those in the art of agriculture, horticulture, and floral design).

The active agents may be delivered to stems, roots, leaves, reproductive tissues, and surrounding soils and water of the plants as grown in fields, forests, managed plots, greenhouses, or climate controlled indoor environments. The compound may be delivered by hand operated devices or mechanized equipment that may or may not be under direct human control. The active agents may be combined with other agents for the purpose of altering the compound's delivery, uptake, solubility, stability, and potency. These methods are well known to those skilled in the art and are not discussed in further detail.

The active agents which constitute the agricultural or horticultural fungicide composition of the present disclosure can be formulated into a variety of forms, such as, but not limited to, emulsifiable concentrates, dustable powders, wettable powders, soluble concentrates, granules, and suspension concentrates, together with various adjuvants, as are common in conventional agricultural preparations. The active agents may be mixed and formulated, or may be separately formulated and then mixed together. Upon use, the preparation may be used as such or as diluted with an appropriate diluent, e.g., water, to a predetermined concentration. Non-limiting examples of the adjuvants (i.e., secondary compounds) which can be used in the agricultural formulations include carriers, emulsifying agents, surfactants, suspending agents, thickeners, stabilizers, dispersants, spreaders, wetting agents, penetrating agents, antifreezing agents, antifoaming agents, and the like. These adjuvants are added appropriately, if necessary. The carriers are classified into solid carriers and liquid carriers. Non-limiting examples of the solid carriers include animal and vegetable powders (e.g., starch, sugar, cellulose powders, cyclodextrin, activated charcoal, soybean powders, wheat powders, chaff powders, wood powders, fish powders, powdery milk, etc.); mineral powders (e.g., talc, kaolin, bentonite, organic bentonite, calcium carbonate, calcium sulfate, sodium hydrogencarbonate, zeolite, diatomaceous earth, white carbon, clay, alumina, silica, sulfur powder, slaked lime, etc.); and the like. Non-limiting examples of the liquid carriers include water, vegetable oils (e.g., soybean oil, cotton seed oil, etc.), animal oils (e.g., beef tallow, whale oil, etc.), alcohols (e.g., ethyl alcohol, ethylene glycol, etc.), ketones (e.g., acetone, methyl ethyl ketone, methyl isobutyl ketone, isophorone, etc.), ethers (e.g., dioxane, tetrahydrofuran, etc.), aliphatic hydrocarbons (e.g., kerosene, lamp oil, liquid paraffin, etc.), aromatic hydrocarbons (e.g., toluene, xylene, trimethylbenzene, tetramethylbenzene, cyclohexane, solvent naphtha, etc.), halogenated hydrocarbons (e.g., chloroform, chlorobenzene, etc.), acid amides (e.g., dimethylformamide, etc.), esters (e.g., acetic acid ethyl ester, fatty acid glycerine esters, etc.), nitriles (e.g., acetonitrile, etc.), sulfur-containing compounds (e.g., dimethyl sulfoxide, etc.), N-methyl-2-pyrrolidone, N,N-dimethylformamide, N,N-dimethylacetamide, and the like. Non-limiting examples of the spreaders include sodium alkylsulfate, sodium alkylbenzene sulfonate, sodium lignin sulfonate, polyoxyethylene glycol alkyl ether, polyoxyethylene lauryl ether, polyoxyethylene alkyl aryl ether, polyoxyethylene sorbitan fatty acid ester and the like. These methods are known to those skilled in the art as described in U.S. Pat. No. 8,741,859.

In another non-limiting embodiment, the active agent may be mixed with other agricultural chemicals (secondary compounds), such as (but not limited to) a fungicide, an insecticide, a miticide, a nematocide, a soil insect pesticide, an antivirus agent, an attractant, an herbicide, or a plant growth regulating agent. The active agents described herein may be combined in any ratio with one or more active agricultural chemicals or inactive agents based on volume or weight to obtain a desired activity. The compounds of the present disclosure may also be combined with other agricultural chemicals including (but not limited to) pesticides and herbicides to form mixtures. The fungicidal compounds of the present disclosure can be applied in conjunction with one or more other agricultural chemicals including (but not limited to) fungicides, herbicides, and pesticides to control a wider variety of undesirable diseases. When used in conjunction with other agricultural chemicals and pest control agent(s), the presently disclosed compounds may be formulated with the other agricultural chemicals and other pest control agent(s), tank-mixed with the other agricultural chemicals and other pest control agent(s), or applied sequentially with the other agricultural chemicals and other pest control agent(s). Such other pest control agents may include those skilled in the art as described in U.S. provisional patent application Ser. Nos. 62/442,904; 61/920,942; and 61/920,946; and in U.S. Pat. No. 8,883,811.

Methods and Results

Figure 2:
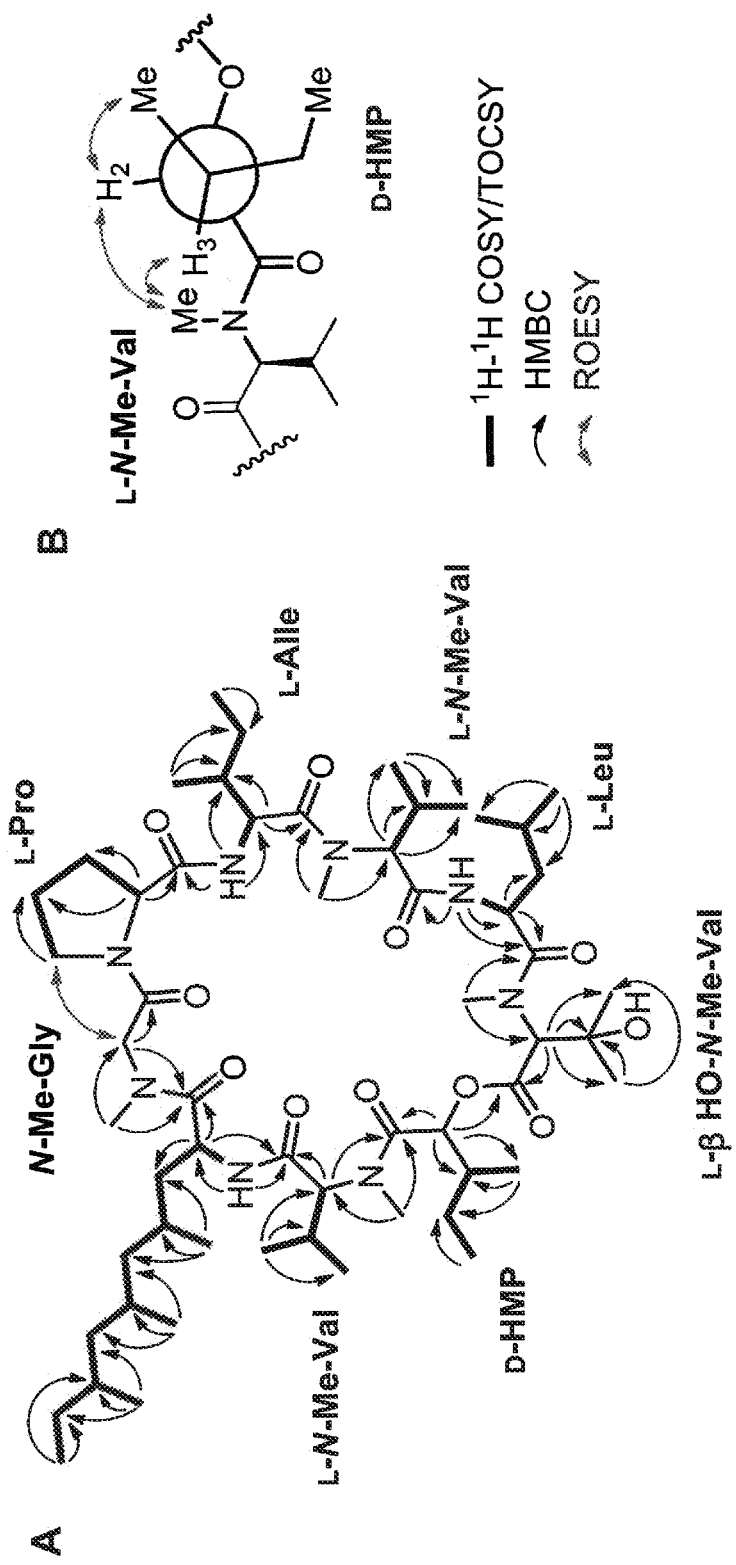
FIG. 2 shows key $^1$H-$^1$H COSY, HMBC, and ROESY (A and B) correlations of 1.

Compound 1 was obtained as a white gel-like semi-solid. Its molecular formula was determined to be $C_{57}H_{102}N_8O_{11}$ based on HRESIMS data. The $^1H$ and $^{13}C$ NMR data for 1 contained a number of features that were indicative of an N-methylated peptide including: three amid NHs appearing in the range of $\delta_H$ 7.5-8.4, four N-methyl resonances spanning $\delta_H$ 3.1-3.3, and nine carbonyl carbons ($\delta_C$ 166.8-177.2), which confirmed the presence of several amide and/or ester groups in the metabolite (see Table 1 in Provisional Application U.S. Ser. No. 62/701,079 filed Jul. 20, 2018). The 2D NMR data ($^1H$-$^1H$ COSY, TOCSY, HSQC, and HMBC; FIG. 2A) were used to initiate the process of identifying the eight amino-acid and one 2-hydroxy-acid residues that were incorporated into 1. These analyses supported the presence of one β-hydroxy-N-methylvaline (βOH-N-Me-Val), one leucine (Leu), two N-methyl-valines (N-Me-Val), one proline (Pro), one N-methyl-glycine (N-Me-Gly), one isoleucine (ile) or allo-isoleucine (Alle), one 2-hydroxy-3-methylpentanoic acid (HMP), and one novel amino acid. Further interpretation of the 1D and 2D NMR data (see Table 1 in Provisional Application U.S. Ser. No. 62/701,079, filed Jul. 20, 2018, and FIG. 2A herein) revealed that the new amino acid residue contained a hydrophobic sidechain that was consistent with a trimethyloctane moiety.

Continued evaluation of the NMR data suggested that metabolite 1 was a cyclic depsipeptide, which was supported based on the presence of a series of HMBC correlations from the α-protons to their respective vicinal carbonyls and from the NH and NCH$_3$ protons to their neighboring carbonyls and α-carbons (FIG. 2A). One exception did occur concerning the linkage between the N-Me-Gly and Pro residues. While no unambiguous HMBC correlations were identified, their respective positions in the compound were inferred based on ROESY correlations between the N-Me-Gly α-proton [$δ_H$ 4.30 (H-28a)] and the Pro δ-protons [$δ_H$ 3.79 and $δ_H$ 3.57 (H-34)] (FIG. 2A). Thus, the bond-line structure of 1 was established as a new cyclic depsipeptide, and it was given, as noted above, the trivial name persephacin (also see FIG. 1). The new amino acid residue in 1, given the name persephanine (9) herein, is shown below.

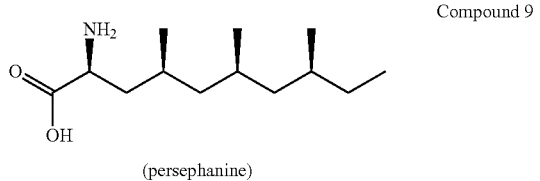 [SMILES: CC[C@H](C)C[C@H](C)C[C@H](C)C[C@H](N)C(=O)O]

Compound 9

(persephanine)

The absolute configuration of 1 was determined by a combination of Marfey's analysis, acidic hydrolysis with further modification of the amino acids, and comparisons of experimental versus computational spectroscopic data ($^{13}$C NMR chemical shifts, ECD spectra, and specific rotation values). Compound 1 was subjected to acidic hydrolysis followed by derivatization with Marfey's reagent. Deuterium chloride (20% by volume in $D_2O$) was used in the process of hydrolyzing 1 to detect if epimerization of the resulting amino acid residues occurred. The FDAA derivatives of the hydrolysate were analyzed by LCMS using several elution conditions (i.e., different sorbents and gradient conditions). The resultant data were used for comparisons with the retention times and masses of the FDAA derivatives for the corresponding L- and D-amino acid standards. An initial set of LCMS runs (17 min gradient over $C_{18}$) provided conditions for the detection of the FDAA derivative of 9 (rt=10.95 min; m/z 480.2 Da [M−H]$^−$) under negative mode conditions, but it proved insufficient for resolving most of the other hydrophobic amino acids (i.e., L- and D-Leu, Ile, Alle, and N-Me-Val). Accordingly, a modified LCMS method was used (45 min gradient over $C_{18}$), which enabled the assignments of the absolute configurations for the L-Pro, L-Leu, and L-N-Me-Val. A third set of LCMS conditions were devised (Lux cellulose-2 column) that afforded the identification of the L-Alle residue. This left the absolute configurations of 9 and βOH-N-Me-Val unresolved, requiring the use of other methods to probe these remaining residues.

Figure 3:
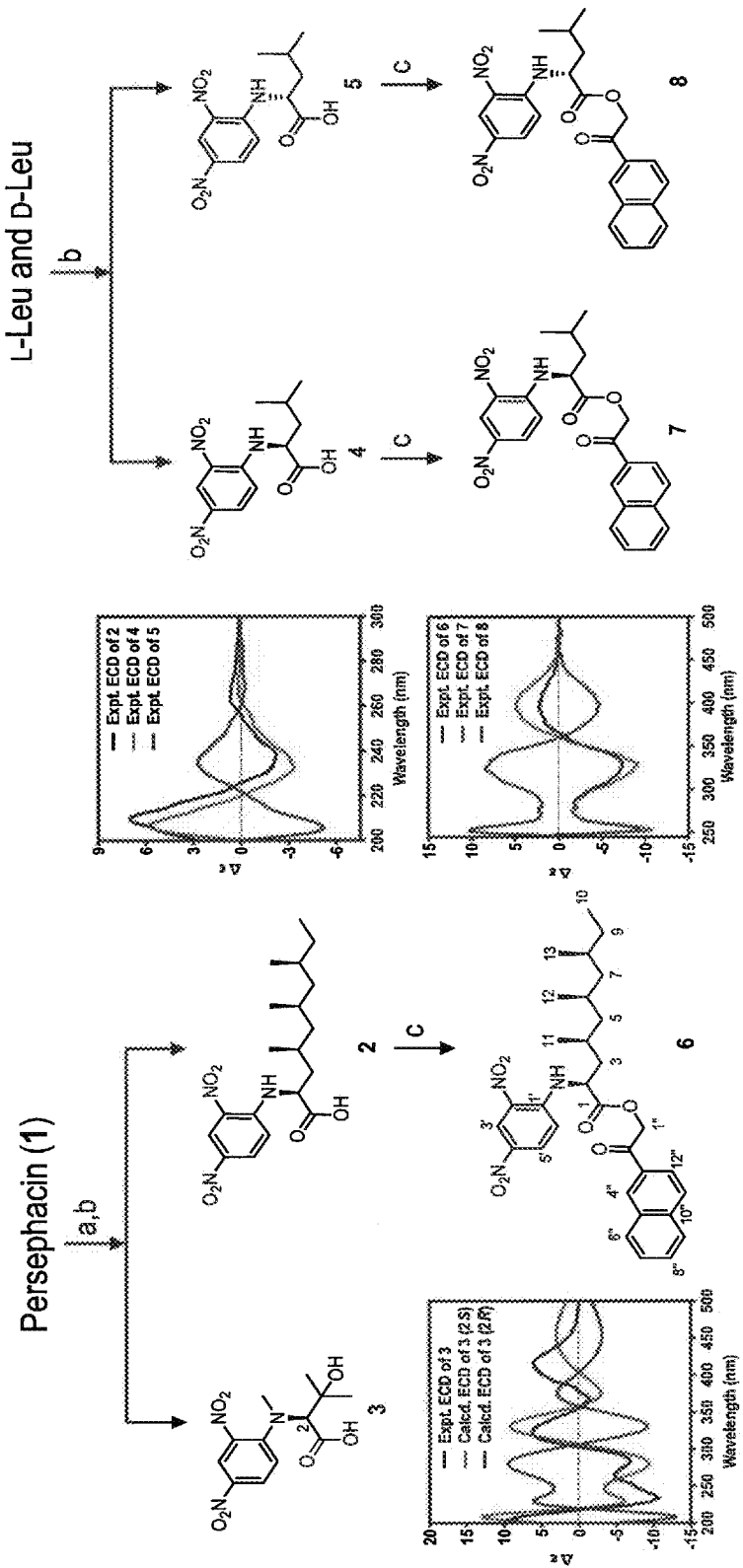
FIG. 3 shows a scheme for chemical derivatization of the hydrolysate of 1 and amino acid standards. The experimental and DFT-calculated [B3LYP/6-31+G(d,p) in gas phase] ECD spectra that were used for absolute configuration analysis are shown.

Compound 1 (30 mg) was hydrolyzed in 6N HCl, and the hydrolysate was derivatized with 1-fluoro-2,4-dinitrobenzene (DNFB)[15] to yield the 2,4-dinitrophenyl (DNP) derivatives 2 and 3 of persephanine and βOH-N-Me-Val, respectively (FIG. 3). The absolute configuration of the α-carbon of the βOH-N-Me-Val residue was determined to be S based on comparisons of the computationally generated ECD spectra of the S and R isomers of 3 with experimentally-derived ECD data (FIG. 3).

Recognizing the structural novelty of residue 9, additional steps were taken to probe its α-carbon configuration. Since compound 2 only contained one UV-active chromophore, and the length of the hydrocarbon sidechain was reasoned to have little bearing on its ECD spectral features, the DNP derivatives of L- and D-Leu (4 and 5, respectively) were prepared as standards for comparative purposes. Compounds 2 and 4 exhibited near identical ECD spectra, supporting a 2S configuration for 9 (FIG. 3). To corroborate this finding, a second esterification step was carried out on 2, 4, and 5 to add an additional chromophore, which yielded products 6-8, respectively. The ECD spectra of 6-8 showed the expected additional Cotton effects and enhanced signal intensities (FIG. 3). Again, the ECD spectrum of 6 provided a close match to the ECD data generated for L-Leu derivative 7. Thus, the absolute configuration of the α-position of persephanine (9) was assigned as S.

Figure 4:
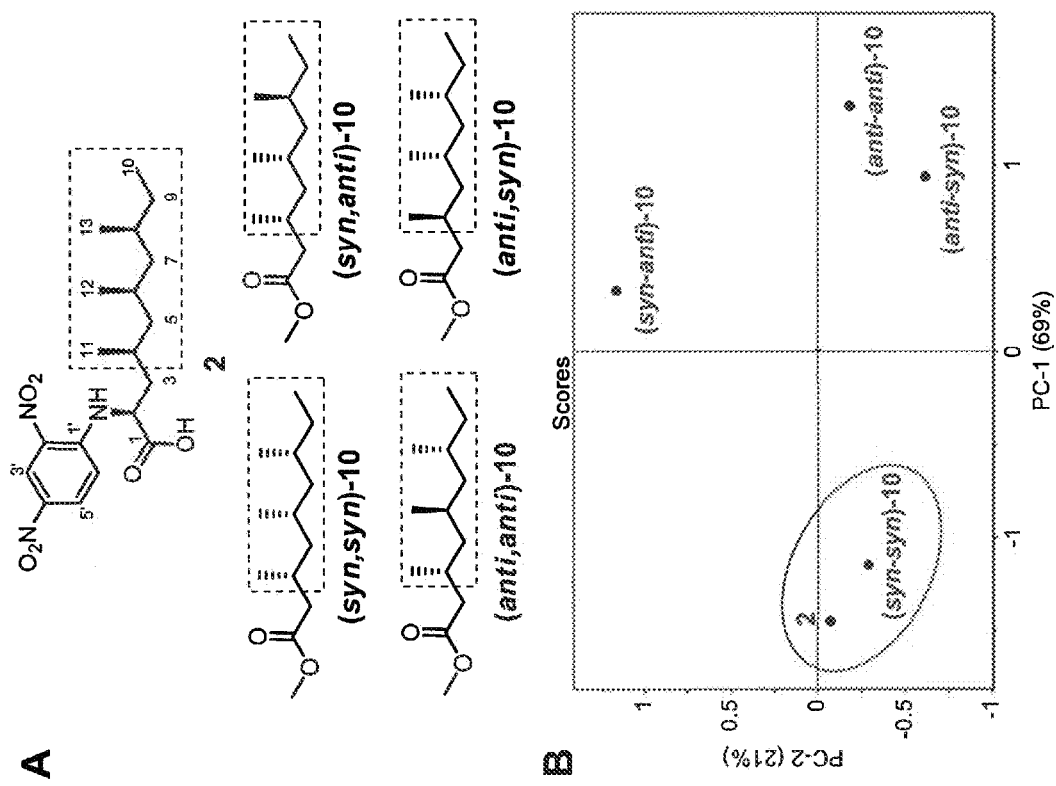
FIG. 4 shows a comparison of the selected $^{13}$C NMR chemical shifts (carbons highlighted in boxes) of 2 and the four stereoisomers of 10 (A) by principle components analysis (B).

To determine the relative configuration of the C-4, C-6, and C-8 methyl groups in 9, the spectroscopic data of four synthetic stereoisomeric compounds [(syn,syn)-, (syn,anti)-, (anti,anti)-, and (anti,trans)-10, FIG. 4A] bearing the same branched aliphatic moieties were examined. A summary of the $^{13}$C NMR chemical shift data for 2 and the four stereoisomers of 10 is illustrated in FIG. 4A (and see Table 2 in Provisional Application U.S. Ser. No. 62/701,079, filed Jul. 20, 2018). Principal component analysis [PCA, using Unscrambler X 10.3 (CAMO Software, Inc.)] revealed strong similarity between the $^{13}$C NMR data for 2 and (syn,syn)-10 (FIG. 4B). Accordingly, it was predicted that the methyl groups present in the side chain of the new amino acid residue bore a syn, syn relative configuration.

Figure 5:
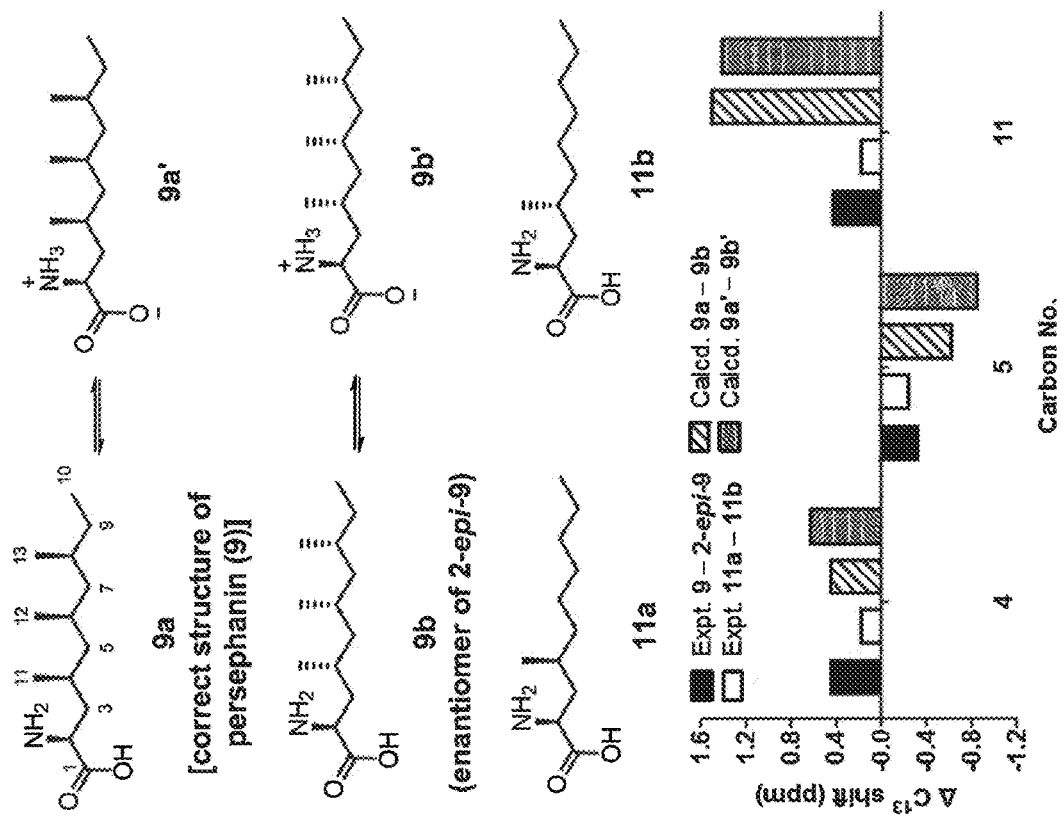
FIG. 5 shows a comparison of the differences among selected experimental (9 vs 2-epi-9 and 11a vs 11b) and calculated (9a vs 9b and 9a' vs 9b') carbon chemical shifts.

Combining these two sets of observations about the stereochemical properties of 9, it was deduced that only one of two possible stereoisomers, 9a or 9b (FIG. 5), represented the absolute configuration of new amino acid. To evaluate the appropriateness of these two possible solutions, 9 was purified from the acidic hydrolysate of 1 using reverse-phase $C_{18}$ HPLC, and its bond-line structure was reconfirmed upon interpretation of its 1D ($^1$H and $^{13}$C) and 2D ($^1$H-$^1$H COSY, HSQC, and HMBC) NMR data. A sample of 9 was partially converted into its α-carbon epimer (2-epi-9), and $^{13}$C NMR data were obtained for the product mixture (see Table 3 in Provisional Application U.S. Ser. No. 62/701,079, filed Jul. 20, 2018). This test revealed significant differences among the chemical shifts attributed to C-4, C-5, and C-11 ($Δ_C$>0.3 ppm) (FIG. 5). To provide a context for interpreting the observed chemical shift differences, NMR data reported for a structurally relevant set of amino-acid epimers, 11a and 11b, were analyzed with regard to how the configurations of the C-4-methyl-groups effected the C-4, and C-5, and C-11 chemical shifts. Upon comparing the C-4 epimeric pairs (11a/11b and 9/2-epi-9), it was noted that C-4, and C-5, and C-11 exhibited similar changes in their respective $^{13}$C NMR chemical shifts (FIG. 5). These results suggested that compounds 9 and 11a shared the same 2,4-syn relative configurations, whereas 2-epi-9 and 11b bore 2,4-anti relative configurations. Considering the results for these stereochemical analyses in their entirety, the absolute configuration of 9 was hypothesized to be 2S,4S,6S,8S.

This hypothesis was further tested by assessing the theoretical $^{13}$C NMR chemical shifts and specific rotation values of 9a, 9b, and their corresponding zwitterions 9a' and 9b', which were obtained via DFT calculations applying the RmPW1PW91 method[20] and IEFPCM solvation model. The computationally-derived $^{13}$C-chemical-shifts differences ($Δδ_{9a}$-$δ_{9b}$ and $Δδ_{9a'}$-$δ_{9b'}$) for C-4, C-5, and C-11 (in DMSO-$d_6$) showed the same trends as were noted in the experimentally-derived data ($Δδ_9$-$δ_{2\text{-}epi\text{-}9}$) (FIG. 5). Additionally, only 9a' was predicted to exhibit a positive specific rotation ([α]$_D$ 10), which was consistent with the observed value ([α]$_D$ 23), whereas negative specific rotation values were predicted for 9a ([α]$_D$ −18), 9b ([α]$_D$ −36), and 9b' ([α]$_D$ −26). Thus, a 2S,4S,6S,8S configuration (9a, FIG. 5) was secured for 9.

With a majority of the stereocenters in 1 assigned, only the 2-hydroxy-3-methylpentanoic acid (HMP) residue's configuration remained to be addressed. An analysis of the ROESY and $^1$H-NMR $^3J_{H-H}$ coupling constant data for 1

Figure 6:
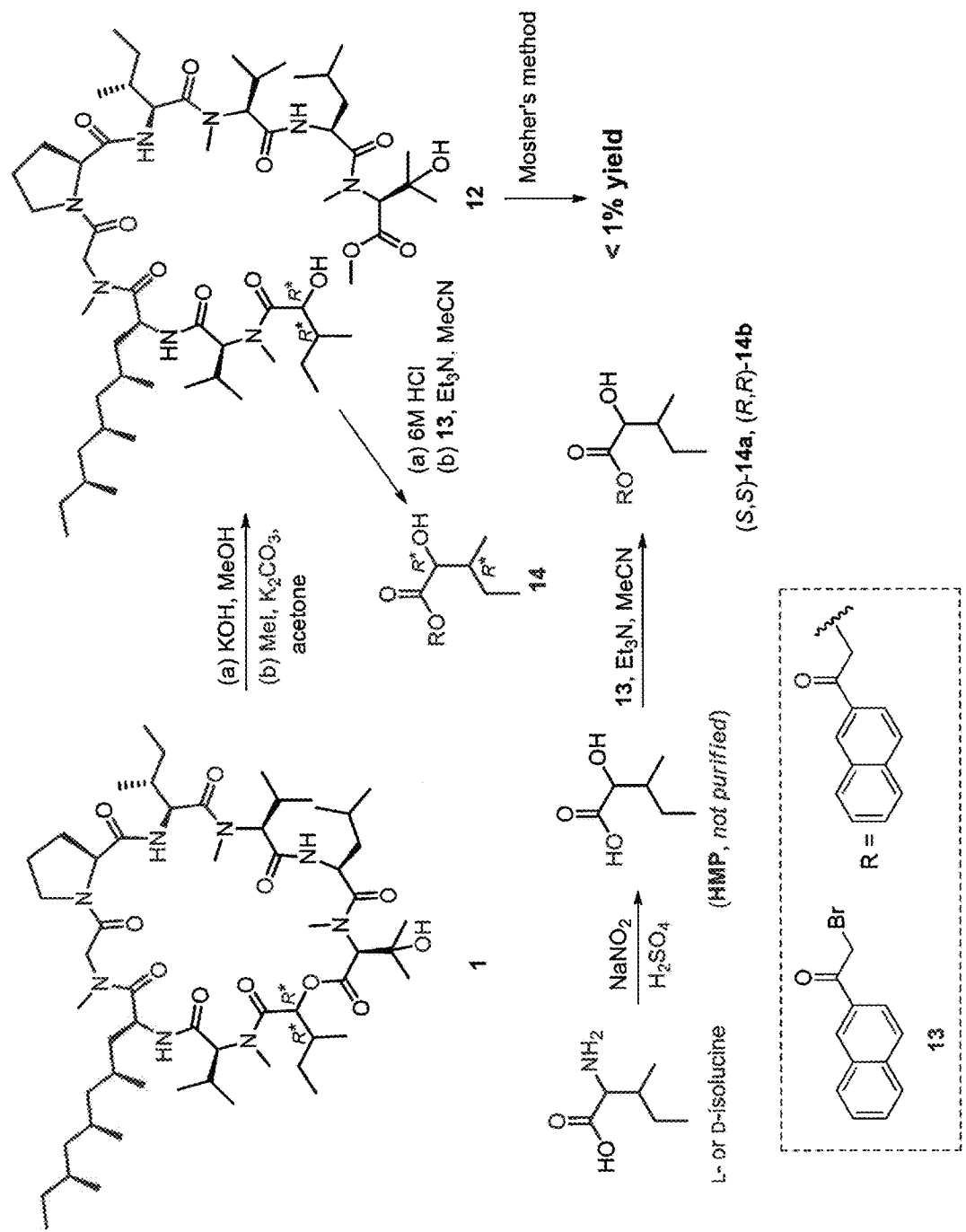
FIG. 6 shows a scheme of hydrolytic Degradation of 1 and Synthesis of 2-Naphthacyl Esters of 2-Hydroxy-3-methyl-pentanoic Acid (HMP) Stereoisomers.

(FIG. 2B) revealed that the C-2/C-3 bond of the HMP residue was rotationally restricted, which presented an opportunity for determining the relative configurations of the HMP C-2 and C-3 stereocenters. The H-2 resonance of HMP showed ROESY correlations between H-3 and $CH_3$-6, whereas no ROEs were observed between H-2 and 2H-4. Both H-2 and H-3 of HMP showed strong ROESY correlations with the N—$CH_3$ protons (δ 3.20) of L-N-Me-Val. Combining these observations with the small value measured for the coupling between H-2/H-3 (J=2.0 Hz), a 2R*,3R* relative configuration was deduced (FIG. 1). To determine the absolute configuration of C-2, Mosher's method was employed. This required that the ester bond of 1 had to be selectively opened by mild alkaline hydrolysis (KOH/MeOH) and the resulting carboxyl group protected by methylation (MeI). A mixture of products was obtained with one of the major components, 12, showing that it had retained the desired L-βOH-N-Me-Val residue (scheme shown in FIG. 6). After several failed attempts to directly react 12 with the (R)-(−)- and (S)-(+)-Mosher's acid chlorides (yields <1%, data not shown), an alternative strategy was devised to ascertain the HMP residue's configuration using chiral HPLC analysis. Compound 12 was subjected to further hydrolysis (6 M HCl), and the resulting hydrolysate underwent esterification with 2-bromo-1-(naphthalen-2-yl) ethan-1-one (13) to generate 14 (FIG. 6). Additionally, the HMP 2-naphthacyl esters, (S,S)-14a and (R,R)-14b, were prepared from L-isoleucine and D-isoleucine, respectively (FIG. 6). Chiral HPLC analysis revealed that 14 coeluted with the prepared standard, (R,R)-14b (FIG. 6); therefore, the absolute configuration of the HMP residue in 1 was determined to be 2R,3R.

Compound 1 is a novel member of the aureobasidin family of antifungal depsipeptides [e.g., aureobasidin A (ABA)]. What sets this new metabolite apart from its naturally occurring antecedents are the drastic structural changes occurring to residues #3 and #4 (refer to FIG. 1 and Table 1 for numbering), which had heretofore been exclusively occupied by aromatic amino acid residues. Like most aureobasidins, ABA contains a Phe residue at position #3 and an N-Me-Phe at position #4. In contrast, metabolite 1 possesses the novel non-polar aliphatic amino-acid residue 9 at position #3 and an N-Me-Gly residue at position #4. These structural changes are significant because previous structural-activity-relationship studies of ABA had revealed three important factors that have hampered this compound's clinical development. First, ABA and its natural analogs exhibit rather good antifungal activities against pathogenic yeast (e.g., *Candida* spp. and *Cryptococcus* spp.), while many important filamentous fungal pathogens, such as *Aspergillus fumigatus*, are not inhibited. The resistance displayed by *A. fumigatus* to ABA was determined to be due to the compound's efflux, which is a common defensive mechanism employed by fungi. Second, studies have shown that the activity spectrum of ABA can be dramatically improved via semisynthetic modifications [e.g., the N-Me-Phe at position #4 was converted to smaller (N-Me-Ala or N-Me-Gly) residues]. Third, when the previously mentioned structural changes at position #4 are combined with modification of the Phe residue at position #3, a broad-spectrum antifungal agent was obtained that exhibits potent activity against a large number of clinical fungal pathogens including *A. fumigatus*. Unfortunately, these modifications can only be achieved at the cost of a 21-step semisynthesis process and in yields of <1%. More recently it was demonstrated that semisynthetic modification of the N-Me-Phe at position #4 in ABA could be achieved in a three-step synthetic process, and this afforded potent ABA analogs with improved activity spectra. Collectively, these results show that the ABA scaffold can be modified at positions #3 and #4 and that these changes can bring about substantial improvements in the antifungal activity profile of this family of natural products. Considering the findings, compound 1 was deemed to be exceptionally promising, because this naturally sourced metabolite contains a novel structural solution to overcoming the bioactivity problems inherent to ABA and its naturally occurring congeners.

To assess how the unique structural features of 1 affected the compound's spectrum of activity, an initial investigation was carried out using a group of 44 clinical yeast isolates (representative of the genera *Candida*, *Kodameae*, and *Saccharomyces*), which was obtained from the U.S. Centers for Disease Control and Prevention (Table 1). Testing revealed that all of the pathogens were highly sensitive to compound 1 including several isolates that are considered emerging drug-resistant yeasts (e.g., *Candida auris*). The median $MIC_{80}$ (the lowest concentration causing prominent growth reduction up to 80%) for compound 1 was 2.5 μM (minimum $MIC_{80}$ value: 0.15 μM, maximum $MIC_{80}$ value: 5 μM), which compared favorably to the standard-of-care drug, amphotericin B (median $MIC_{80}$ value: 1.25 μM, minimum $MIC_{80}$ value: 0.15 μM, maximum $MIC_{80}$ value: 2.5 μM). This is noteworthy because amphotericin B, although it is a first-line treatment for many types of fungal infections, carries with it many clinically-limiting side-effects, including a substantial risk for severe nephrotoxicity. While animal tests have yet to be performed with 1, it was encouraging to observe that the new natural product exhibited minimal in vitro toxicity toward human cells ($LC_{50}$ value of 30 μM against both HepG2 and Ect1/E6E7 cell lines).

TABLE 1

Antifungal Activities Of 1 and Amphotericin B (AMB) Against Selected Clinical Yeast Pathogens

| $MIC_{80}$ (μM)[a] | 1 | AMB |
|---|---|---|
| *Candida albicans* 1 | 2.5 | 0.6 |
| *Candida albicans* 3 | 2.5 | 0.6 |
| *Candida albicans* 5 | 1.25 | 0.6 |
| *Candida albicans* 8 | 0.6 | 0.6 |
| *Candida albicans* 10 | 2.5 | 0.6 |
| *Candida albicans* 14 | 0.6 | 1.25 |
| *Candida albicans* 21 | 1.25 | 0.6 |
| *Candida albicans* 24 | 0.6 | 1.25 |
| *Candida albicans* 30 | 5 | 2.5 |
| *Candida glabrata* 2 | 0.15 | 0.3 |
| *Candida glabrata* 4 | 1.25 | 1.25 |
| *Candida glabrata* 11 | 0.6 | 0.3 |
| *Candida glabrata* 16 | 0.3 | 0.15 |
| *Candida glabrata* 17 | 0.15 | 0.3 |
| *Candida glabrata* 20 | 0.3 | 0.6 |
| *Candida glabrata* 22 | 0.6 | 0.3 |
| *Candida parapsilosis* 7 | 2.5 | 2.5 |
| *Candida parapsilosis* 9 | 2.5 | 2.5 |
| *Candida parapsilosis* 15 | 2.5 | 2.5 |
| *Candida parapsilosis* 18 | 1.25 | 1.25 |
| *Candida parapsilosis* 23 | 2.5 | 1.25 |
| *Candida parapsilosis* 28 | 2.5 | 1.25 |
| *Candida kefyr* 12 | 1.25 | 0.3 |
| *Candida krusei* 25 | 1.25 | 1.25 |
| *Candida tropicalis* 13 | 0.625 | 0.15 |
| *Candida auris* 381[b] | 2.5 | 1.25 |
| *Candida auris* 382[b] | 2.5 | 1.25 |
| *Candida auris* 383[b] | 2.5 | 2.5 |
| *Candida auris* 384[b] | 2.5 | 2.5 |
| *Candida auris* 385[b] | 2.5 | 2.5 |
| *Candida auris* 386[b] | 2.5 | 2.5 |
| *Candida auris* 387[b] | 2.5 | 2.5 |

TABLE 1-continued

Antifungal Activities Of 1 and Amphotericin B (AMB)
Against Selected Clinical Yeast Pathogens

| $MIC_{80}$ (μM)[a] | 1 | AMB |
|---|---|---|
| Candida auris 388[b] | 2.5 | 2.5 |
| Candida auris 389[b] | 2.5 | 5 |
| Candida auris 390[b] | 2.5 | 2.5 |
| Candida duobushaemulonii 391[b] | 2.5 | 5 |
| Candida duobushaemulonii 392[b] | 2.5 | 5 |
| Candida haemulonii 393[b] | 0.3 | 5 |
| Candida duobushaemulonii 394[b] | 2.5 | 5 |
| Kodameae ohmeri 396[b] | 2.5 | 1.25 |
| Candida krusei 397[b] | 2.5 | 2.5 |
| Candida lusitaniae 398[b] | 2.5 | 0.6 |
| Saccharomyces cerevisiae 399[b] | 2.5 | 2.5 |
| Saccharomyces cerevisiae 400[b] | 2.5 | 1.25 |

[a]The $MIC_{80}$ was defined as the lowest concentration causing prominent growth reduction up to 80%.
[b]Emerging opportunistic multidrug-resistant yeast pathogens.

Next, compound 1 was tested against a taxonomically diverse panel of pathogenic fungi wherein its activity was evaluated in direct comparisons to ABA, as well as three clinical antifungal agents (i.e., amphotericin B, caspofungin, and itraconazole) (Table 2). Metabolite 1 showed itself to be remarkably effective against most of the fungal pathogens, with its antifungal action against *Cryptococcus neoformans* being particularly outstanding ($MIC_{80}$ value: 0.6 μM, MFC value: 2.5 μM). Notably, these results also demonstrated that unlike ABA, metabolite 1 is a potent and broad-spectrum inhibitor of *A. fumigatus*, as well as several other Aspergilli (median $MIC_{80}$ value: 2.5 μM, minimum $MIC_{80}$ value: 1.25 μM, maximum $MIC_{80}$ value: 2.5 μM).

Given that compound 1 contains a large number of hydrophobic amino acid residues that might promote non-specific protein binding resulting in a loss of in vivo activity, the efficacy of the compound was tested in the presence of blood serum against four fungal pathogens (*C. albicans*, *C. auris*, *C. neoformans*, and *A. fumigatus*) (Table 3). Similar to the positive control, amphotericin B, compound 1 showed no loss of activity when 5% and 10% by volume serum was added to the fungal culture medium. This suggests that non-specific protein binding will likely not be a limiting factor for the in vivo application of 1.

TABLE 3

The Effect of Serum on the Antifungal Activities
of 1 and Amphotericin B (AMB)

| | 1 | | | AMB | | |
|---|---|---|---|---|---|---|
| $MIC_{80}$ (μM) | 0%[a] | 5%[a] | 10%[a] | 0%[a] | 5%[a] | 10%[a] |
| Candida albicans SC5314 | 0.6 | 0.15 | 0.3 | 0.6 | <0.15 | <0.15 |
| Candida auris 381 | 1.25 | 1.25 | 1.25 | 2.5 | <0.15 | 0.3 |
| Cryptococcus neoformans H99 | 0.6 | <0.15 | <0.15 | 1.25 | <0.15 | <0.15 |
| Aspergillus fumigatus ATCC MYA-3627 | 2.5 | 2.5 | 2.5 | 2.5 | <0.07 | 0.15 |

[a]Serum concentration (v/v) in the fungal growth medium.

General Methods

Optical rotations were measured on a Rudolph Research Autopol III automatic polarimeter. UV data were measured with a Hewlett Packard 8454A diode array spectrophotometer. NMR data were obtained on Varian VNMR spectrometers (400 and 500 MHz for $^1H$, 100 and 125 MHz for $^{13}C$) with broadband and triple resonance probes. Electrospray-ionization mass spectrometry data were collected on an Agilent 6538 high-mass-resolution QTOF mass spectrom-

TABLE 2

Antifungal Activities of 1 and Standard Antifungal Compounds
Against Selected Fungal Pathogens

| | $MIC_{80}$[a] (μM) | | | | | $MFC$[b] (μM) | | | | |
|---|---|---|---|---|---|---|---|---|---|---|
| | 1 | ABA | AMB | CASP | ITC | 1 | ABA | AMB | CASP | ITC |
| Candida albicans SC5314 | 0.3 | 0.3 | 0.6 | 0.03 | 0.125 | 1.25 | 0.6 | 2.5 | 0.625 | >10 |
| Candida albicans ATCC 10231 | 0.6 | 0.6 | 0.6 | 0.03 | 0.06 | 1.25 | 2.5 | 2.5 | 5 | >10 |
| Candida parapsilosis ATCC 22019 (Y-12969) | 2.5 | 1.25 | 1.25 | 0.3 | 0.6 | 2.5 | 2.5 | 5 | 1.25 | 5 |
| Candida tropicalis ATCC750 (Y-12699) | 1.25 | 0.6 | 1.25 | 0.03 | 0.6 | 2.5 | 0.6 | 2.5 | 0.15 | >10 |
| Candida krusei ATCC 6258 (Y-7179) | 1.25 | 1.25 | 2.5 | 0.15 | 0.6 | 2.5 | 2.5 | 5 | 0.3 | 2.5 |
| Cryptococcus neoformans H99 | 0.6 | 2.5 | 1.25 | >10 | 0.6 | 2.5 | 2.5 | 2.5 | >10 | >10 |
| Aspergillus fumigatus MYA 3627 | 2.5 | >10 | 2.5 | 0.07 | 5 | 5 | >10 | 2.5 | >10 | >10 |
| Aspergillus fumigatus NRRL6113 | 2.5 | >10 | 2.5 | >10 | 1.25 | 5 | >10 | 10 | >10 | >10 |
| Aspergillus fumigatus NRRL5109 | 2.5 | >10 | 2.5 | >10 | 1.25 | 5 | >10 | 5 | >10 | 10 |
| Aspergillus flavus NRRL485 | 1.25 | >10 | 5 | >10 | 0.15 | >10 | >10 | 10 | >10 | 0.6 |
| Aspergillus niger FGSC A732 | 1.25 | 5 | 0.6 | 0.06 | 2.5 | >10 | >10 | 2.5 | >10 | 5 |
| Aspergillus terreus 191A6 | 2.5 | 2.5 | 2.5 | 0.125 | 0.6 | >10 | >10 | 10 | >10 | 2.5 |
| Curvularia lunata NRRL6409 | 0.3 | 0.6 | 0.3 | 5 | 2.5 | 0.6 | 1.25 | 2.5 | 5 | 5 |
| Rhizopus oryzae FGSC 9543 | >10 | >10 | 0.3 | >10 | 0.6 | >10 | >10 | 0.3 | >10 | 0.6 |
| Mucor circinelloides 235C7 | >10 | >10 | 1.25 | >10 | 10 | >10 | >10 | 1.25 | >10 | >10 |
| Fusarium solani 243G2 | 1.25 | 5 | 1.25 | 0.15 | 2.5 | 2.5 | >10 | 1.25 | >10 | 5 |
| Paecilomyces lilacinus 165E10 | 2.5 | 5 | >10 | >10 | 2.5 | >10 | >10 | >10 | >10 | 1.25 |
| Hamigera insecticola NRRL35442 | 0.6 | 0.6 | 2.5 | 0.06 | 0.3 | 5 | >10 | 10 | >10 | 1.25 |

[a]The $MIC_{80}$ was defined as the lowest concentration causing prominent growth reduction up to 80%.
[b]The MFC was defined as the lowest concentration of active compound that reduced the viability of the initial fungal inoculum by at least 99.9%.
Standard compounds: ABA (aureobasidin A), AMB (amphotericin B), CASP (caspofungin), ITC (itraconazole).

eter. Preparative HPLC separations were performed on a Shimadzu system using a SCL-10A VP controller and a Gemini 5 μm $C_{18}$ column (110 Å, 250×21.2 mm) or a Kinetex 5 μm biphenyl column (110 Å, 250×21.2 mm) with the flow rate of 10 mL/min. Semi-preparative HPLC separations were performed on a Waters 1525 system using a 2998 PDA detector and a Gemini 5 µm $C_{18}$ column (110 Å, 250×10.0 mm) with the flow rate of 4 mL/min. The experimental ECD spectrum was measured with a Jasco J715 circular dichroism spectrometer. All solvents were of ACS grade or better.

Purification of Persephacin (Compound 1)

Efforts to sample endophytic fungi from the Norman, Okla., U.S.A. area resulted in the identification of an unusual fungus (deep red, compact colony) that appeared to block the growth of other nearby fungi emerging from *Poplar* sp. leaf samples. Spores of *Elsinoë* sp. (Synonym: *Sphaceloma* sp.) were inoculated into 12 L of enriched PDB media (40 g/L dried mashed potato, 20 g/L glucose). Upon culturing for three weeks on a shaker, the resulting culture broth was extracted three times with EtOAc. The combined crude extract (25 g) was subjected to HP20ss vacuum column chromatography (eluted with gradients of 30%, 50%, 70%, and 100% MeOH in $H_2O$) to generate four fractions. Fraction Fr. 4 was further separated by a Sephadex LH20 column (MeOH as eluent) to give 16 fractions. Fractions that contained the antifungal principle were combined and subjected to two further steps of preparative HPLC (Gemini 5 µm $C_{18}$ column 250*21.2 mm, 95% MeCN in $H_2O$, and then Kinetex 5 µm biphenyl column 250*21.2 mm, 90% MeOH in $H_2O$) to yield compound 1 (95 mg).

Persephacin (1): white solid; $[\alpha]^{20}_D$ −211 (c 1.25, MeOH); UV (MeOH) $\lambda_{max}$ (log ε) 230 (4.65); CD (MeOH) $\lambda_{max}$ (Δε) 223 (−113); $^1H$ and $^{13}C$ NMR data, see Table 1; HRESIMS m/z 1097.7586, [M+Na]$^+$ (calcd for $C_{57}H_{102}N_8NaO_{11}$, 1097.7560).

Marfey's Analysis of FDAA Derivatives of Compound 1

Compound 1 (500 µg) in deuterium chloride (20% w/w in $D_2O$, 200 µL) was heated at 100° C. for 24 h. The hydrolysate was dried down under $N_2$ and then treated with 1 M $NaHCO_3$ (40 µl) and 1% FDAA/acetone (200 µl) at 70° C. for 1 h. The reactants were neutralized with 1 M HCl (40 µl), and diluted with $CH_3CN$ (200 µl) prior to LC-MS analysis. FDAA derivatives of amino acid standards were prepared in a similar manner. Aqueous solutions of amino acid standards (50 mM, 50 µl) were reacted, neutralized, and diluted following the same procedure as described.

Acidic Hydrolysis of 1 and Derivatization of the Hydrolysate and Amino Acid Standards. Compound 1 (30 mg) in 6M HCl (10 mL) was heated at 100° C. for 24 h. The hydrolysate was dried down in vacuo and treated with 1-fluoro-2,4-dinitrobenzene (DNFB, 300 µl) and $NaHCO_3$ (300 mg) in 50% EtOH (8 mL). The reactants were stirred at 70° C. for 1 h before being neutralized with 1 M HCl and the solvent was removed in vacuo. Further purification of the DNP derivatives was achieved by semipreparative HPLC (Gemini 5 µm C18 column 250*10 mm, 75% MeCN in $H_2O$ containing 0.1% TFA) to afford compounds 2 (6.5 mg) and 3 (0.4 mg). DNP derivatives of standard L-Leu (50 mg) and $_D$-Leu (50 mg) were prepared in a similar manner to yield the DNP derivatives 4 (110 mg) and 5 (115 mg), respectively.

N-(2,4-Dinitrophenyl)-L-persephanine (2): yellow solid; $[\alpha]^{20}_D$ −93 (c 0.3, MeOH); UV (MeOH) $\lambda_{max}$ (log ε) 255 (4.06), 344 (4.20); CD (MeOH) $\lambda_{max}$ (Δε) 210 (7.0), 238 (−2.2); $^1H$ and $^{13}C$ NMR data, see Tables 2 and 3; HRESIMS m/z 394.1987, [M−H]$^-$ (calcd for $C_{19}H_{28}N_3O_6$, 394.1984).

3-Hydroxy-N-(2,4-dinitrophenyl)-N-methyl-L-valine (3): yellow solid; $[\alpha]^{20}_D$ 286 (c 0.025, MeOH); UV (MeOH) $\lambda_{max}$ (log ε) 223 (4.35), 370 (3.99); CD (MeOH) $\lambda_{max}$ (Δε) 203 (9.6), 232 (−10.8), 283 (−7.0), 317 (5.9), 368 (−1.6), 416 (6.1); $^1H$ and $^{13}C$ NMR data, see Tables 2 and 3; HRESIMS m/z 312.0846, [M−H]$^-$ (calcd for $C_{12}H_{14}N_3O_7$, 312.0837).

N-(2,4-Dinitrophenyl)-L-leucine (4): yellow solid; $[\alpha]^{20}_D$ −43 (c 0.4, MeOH); UV (MeOH) $\lambda_{max}$ (log ε) 255 (4.13), 343 (4.27); CD (MeOH) $\lambda_{max}$ (Δε) 207 (5.8), 233 (−3.2); $^1H$ and $^{13}C$ NMR data, see Tables 2 and 3; HRESIMS m/z 290.0902, [M−H]$^-$ (calcd for $C_{12}H_{14}N_3O_6$, 296.0888).

N-(2,4-Dinitrophenyl)-D-leucine (5): yellow solid; $[\alpha]^{20}_D$ 36 (c 0.65, MeOH); UV (MeOH) $\lambda_{max}$ (log ε) 255 (4.08), 343 (4.21); CD (MeOH) $\lambda_{max}$ (Δε) 206 (−5.1), 235 (2.7); $^1H$ and $^{13}C$ NMR data, see Tables 2 and 3; HRESIMS m/z 290.0900, [M−H]$^-$ (calcd for $C_{12}H_{14}N_3O_6$, 296.0888).

The DNP derivative 2 (6 mg, 1 eq) was further treated with 2-bromo-2'-acetonaphthone (11 mg, 3 eq) and $Et_3N$ (50 µl) in MeCN (2 mL). The reactants were stirred at 25° C. overnight and subjected to semipreparative HPLC (Gemini 5 µm $C_{18}$ column 250*10 mm, 95% MeCN in $H_2O$ containing 0.1% formic acid) to afford diprotected derivative 6 (6.7 mg). The diprotected derivatives of L-Leu and D-Leu were prepared from 4 (8 mg) and 5 (13 mg) in a similar manner to yield 7 (9.2 mg) and 8 (14.5 mg), respectively.

N-(2,4-Dinitrophenyl)-L-persephanine, 2-(naphthalen-2-yl)-2-oxoethyl ester (6): yellow solid; $[\alpha]^{20}_D$ −55 (c 0.34, MeOH); UV (MeOH) $\lambda_{max}$ (log ε) 248 (4.90), 341 (4.52); CD (MeOH) $\lambda_{max}$ (Δε) 206 (7.7), 233 (−2.8), 244 (4.4), 252 (−9.2), 327 (−7.2), 397 (2.3); $^1H$ and $^{13}C$ NMR data, see Tables 2 and 3; HRESIMS m/z 562.2557, [M−H]$^-$ (calcd for $C_{31}N_{36}N_3O_7$, 562.2559).

N-(2,4-Dinitrophenyl)-L-leucine, 2-(naphthalen-2-yl)-2-oxoethyl ester (7): yellow solid; $[\alpha]^{20}_D$ −42 (c 0.38, MeOH); UV (MeOH) $\lambda_{max}$ (log ε) 248 (4.84), 341 (4.45); CD (MeOH) $\lambda_{max}$ (Δε) 210 (1.2), 227 (−4.0), 253 (−10.5), 329 (−9.2), 392 (5.2); $^1H$ and $^{13}C$ NMR data, see Tables 2 and 3; HRESIMS m/z 464.1465, [M−H]$^-$ (calcd for $C_{24}H_{22}N_3O_7$, 464.1463).

N-(2,4-Dinitrophenyl)-D-leucine, 2-(naphthalen-2-yl)-2-oxoethyl ester (8): yellow solid; $[\alpha]^{20}_D$ −41 (c 0.70, MeOH); UV (MeOH) $\lambda_{max}$ (log ε) 248 (4.83), 341 (4.45); CD (MeOH) $\lambda_{max}$ (Δε) 214 (−2.1), 228 (4.6), 241 (−3.6), 252 (10.2), 324 (8.4), 397 (−4.9); $^1H$ and $^{13}C$ NMR data, see Tables 2 and 3; HRESIMS m/z 464.1463, [M−H]$^-$ (calcd for $C_{24}H_{22}N_3O_7$, 464.1463).

Purification of L-Persephanine (9) from the Acidic Hydrolysate of 1.

The acidic hydrolysate was prepared from 1 (100 mg) as previously described. Solvent in the hydrolysate was removed in vacuo, and the residue was extracted with acetone (10 mL). The acetone was removed in vacuo and extracted again with MeCN (10 mL). The resulting MeCN-soluable material was dissolved in MeOH and purified by semipreparative HPLC (Gemini 5 µm $C_{18}$ column 250*10 mm, 65% MeOH in $H_2O$ containing 0.1% TFA) to afford compound 9 (8.5 mg).

L-Persephanine (9): white solid; $[\alpha]^{20}_D$ 23 (c 0.4, MeOH); $^1H$ and $^{13}C$ NMR data, see Tables 2 and 3; HRESIMS m/z 228.1972, [M−H]$^-$ (calcd for $C_{13}H_{26}NO2$, 228.1969).

Epimerization of 9.

Compound 9 (2.0 mg) in 500 µL acetic acid was treated with 0.2 µL salicylaldehyde. The reactants were stirred at 100° C. for 1 h and the solvent removed in vacuo. The residue was dissolved in MeOH and further purified by semipreparative HPLC (Gemini 5 µm C18 column 250*10 mm, 70% MeOH in $H_2O$ containing 0.1% TFA) to afford an epimeric mixture (2.2 mg) of 9 and 2-epi-9.

Mild Alkaline Hydrolysis of 1 and Methylation of the Products.

Compound 1 (25 mg) was stirred overnight in 1 M methanolic KOH (2.5 mL) at room temperature. The reactants were neutralized with 1 M HCl and the solvent removed in vacuo. The organic residue was suspended in 1.5 mL acetone and 6 mg $K_2CO_3$ and 90 μL MeI were added. The reactants were stirred overnight at room temperature. Solvent was removed from the resulting mixture, and product purification was carried out by semipreparative HPLC (Gemini 5 μm C18 column 250*10 mm, 98% MeCN in $H_2O$ containing 0.1% formic acid) to afford 12 (2.5 mg).

Compound 12: HRESIMS m/z 1129.7825, $[M+Na]^+$ (calcd for $C_{58}H_{106}N_8NaO_{12}$, 1129.7822).

Synthesis of 2-Naphthacyl Esters of 2-Hydroxy-3-methylpentanoic Acid (HMP) Stereoisomers.

The acidic hydrolysate of 12 (1 mg) was prepared under the same conditions as previously described for 1. The hydrolysate was mixed with 2-bromo-2'-acetonaphthone (6 mg) and $Et_3N$ (20 μL) in 1 mL MeCN. After stirring overnight at room temperature, the mixture was directly subjected to chiral HPLC and LCMS analysis.

The (S,S)-HMP and (R,R)-HMP standards were prepared by treating L-isoleucine and D-isoleucine, respectively, with 1 M $H_2SO_4$ (0.8 mL) and $NaNO_2$ (55 mg) at 0° C. The reactants were stirred for 3 h at 0° C. and then stirred overnight at room temperature. Extraction with $Et_2O$ provided the crude (S,S)-HMP and (R,R)-HMP products, which were separately stirred overnight with 2-bromo-2'-acetonaphthone (100 mg) and $Et_3N$ (50 μL) in 3 mL MeCN. Purification of the products by preparative HPLC (Gemini 5 μm C18 column 250*21.2 mm, 65% MeCN in $H_2O$ containing 0.1% TFA) yielded the 2-naphthacyl esters (S,S)-14a (37 mg) and (R,R)-14b (39 mg).

(S,S)-14a: colorless gel; $[\alpha]^{20}_D$ 11 (c 1.4, MeOH); (R,R)-14b: colorless gel; $[\alpha]^{20}_D$ −10.8 (c 2.0, MeOH); $^1H$ NMR (400 MHz, $CDCl_3$) δ 8.42 (1H, s), 7.92 (5H, m), 7.60 (2H, m), 5.63 (1H, d, J=16.2 Hz), 5.52 (1H, d, J=16.2 Hz), 4.32 (1H, d, J=3.8 Hz), 2.70 (1H, br s), 1.99 (1H, m), 1.57 (1H, m), 1.34 (1H, m), 1.09 (1H, d, J=6.9 Hz), 0.97 (1H, t, J=7.8 Hz); $^{13}C$ NMR (100 MHz, $CDCl_3$) δ 191.4, 174.6, 136.1, 132.4, 131.4, 129.7 (2C), 129.1, 129.0, 128.0, 127.3, 123.3, 75.2, 66.7, 39.3, 23.8, 15.4, 11.9; HRESIMS m/z 301.1436, $[M+H]^+$ (calcd for $C_{18}H_{21}O_4$, 301.1434).

Computational Details

Conformational analyses were carried out using ComputeVOA™ v1.1 software. Geometry, frequency, $^{13}C$ NMR, ECD, and specific rotation calculations were applied at the DFT and TD-DFT levels [B3LYP or RmPW1PW91 functional/6-31+G(d,p) or 6-31G(d,p) or DGDZVP basis set] using Gaussian'09 carried out in gas phase or in MeOH or DMSO (IEFPCM solvation model). For each substance, subsets of the lowest energy conformers were obtained by selecting only those conformers with energies predicted to be within 3.0 kcal/mol of their respective lowest-energy conformers. The ECD spectra, $^{13}C$ NMR data, and specific rotation values of these conformers were summed after a Boltzmann statistical weighting. Single UV and ECD spectra of the calculated conformers were determined and combined by SpecDis 1.71 using a sigma value of 0.2~0.3 eV. After applying a UV-shift correction, the computed ECD spectra were compared with the experimentally determined ECD curves.

Antifungal Assays

The antifungal activities of the compounds were assessed using the method described in the NCCLS M38-A guidelines with following modifications. Fungi were cultured on PDA plate (potato dextrose agar, Becton Dickinson and Company) at 28° C. for 6-10 days. The spores or cells were collected from Petri plates and diluted in RPMI 1640 medium (Sigma Chemical Corporation) buffered to pH 7.0 with MOPS (0.165 M, Sigma). Test compounds were prepared in DMSO at stock concentrations of 10 mM before being serially diluted in 50 μL RPMI 1640 plus MOPS medium for testing. Aliquots of the inocula were added to the medium containing the diluted compounds or vehicle (≤1% by vol.). After 48 h of incubation at 35° C., the optical densities of fungi were measured using a microplate reader (Infinite M200, Tecan Group Ltd.). The minimum inhibitory concentration ($MIC_{80}$) was defined as the lowest concentration causing prominent growth reduction that was at least 80% of control samples. Minimum fungicidal concentrations (MFC) of compounds were evaluated by plating all cells from the tested wells on potato dextrose agar (PDA). The MFC was defined as the lowest concentration of active compound that reduced the viability of the initial fungal inoculum by ≥99.9%. In order to evaluate the effect of serum, 5% and 10% by volume serum were added in RPMI 1640 plus MOPS medium.

Mammalian Cell Cytotoxicity Assays

Cell cytotoxicity was tested against the human liver cancer cell line HepG2 and the HPV-immortalized ectocervical epithelium cell line Ect1/E6E7. The HepG2 cells were cultured in the EMEM medium supplemented with 5% FetalClone III and penicillin/streptomycin (5 Units/mL, 50 ug/mL). The Ect1/E6E7 cells were grown in the RPMI 1640 medium supplemented with 5% FetalClone III, EGF (10 ng/mL Novoprotein #C029), and penicillin/streptomycin (5 Units/mL, 50 ug/mL). For the assays, 5,000 HepG2 or Ect1/E6E7 cells were seeded into each well of a 96-well plate and allowed to attach overnight in a 37° C. humidified incubator. The next day, test compounds were diluted in DMSO, added to the wells at a final DMSO concentration of 0.5% and cells were incubated for an additional 48 hours. Cell viability was determined by the Calcein and Hoechst Assay on the Perkin Elmer Operetta. In each assay, 5 μL of the fluorescent dyes (40 μM calcein AM and 160 μM Hoechst 33342 in DMSO) and 25 μL PBS were added into each well. Plates were incubated for 30 minutes and then analyzed on the Operetta. The Harmony software was used to calculate the whole-cell area by finding all the Hoechst-labeled nuclei. The live and dead cells were assessed based on a threshold of the green calcein fluorescence. The live cells contained active esterases capable of cleaving the AM group from calcein AM and thus glowed a bright fluorescent green.

Bioactivity of Persephacins against Pathogenic Fungi

Figure 7:
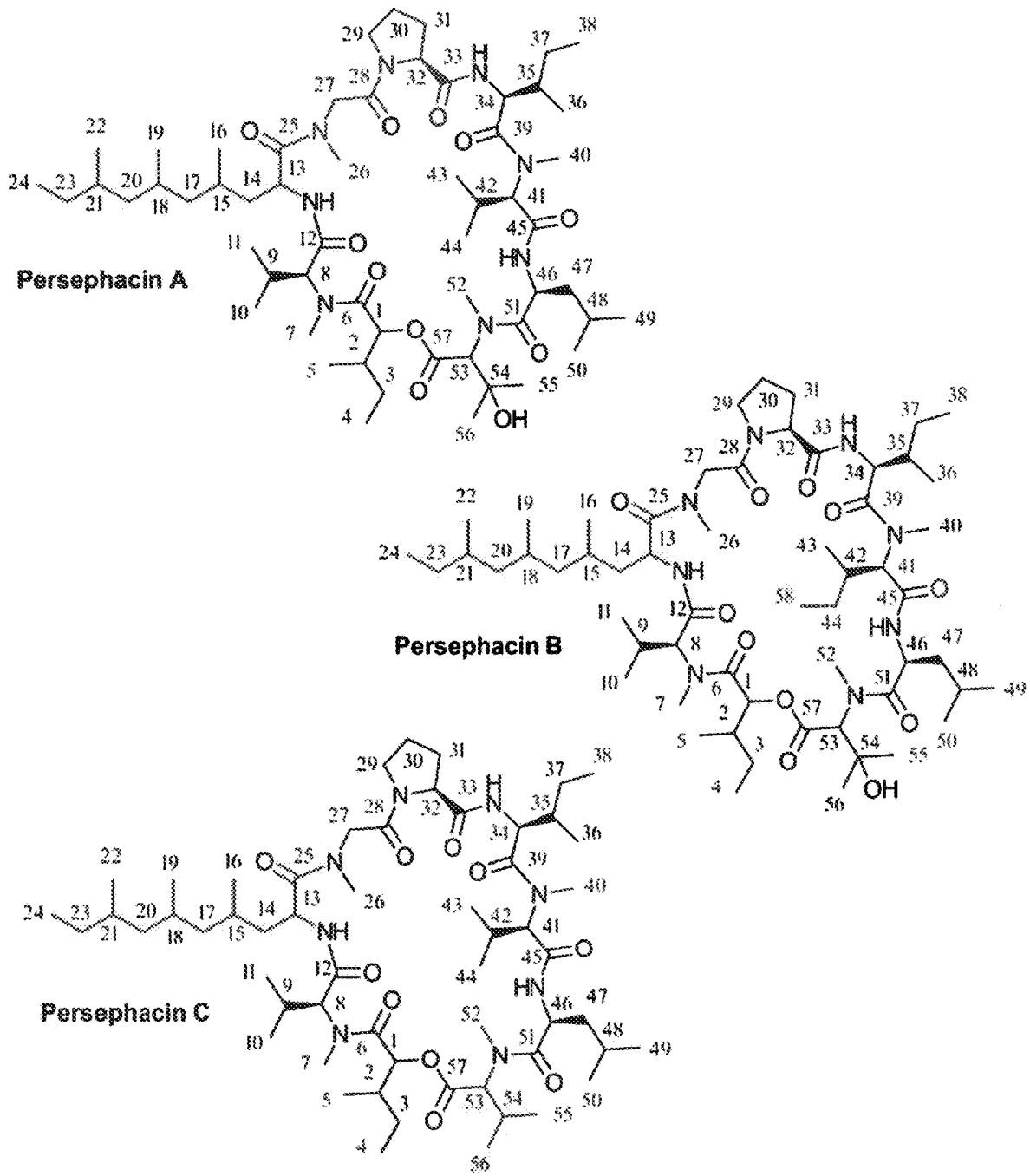
FIG. 7 shows structures of three persephacins constructed in accordance with the present disclosure: A (a.k.a., 118A), B, and C, isolated herein.

Three different forms of persephacins were isolated. FIG. 7 shows structures of the three isolated persephacins, designated herein as persephacin A (also referred to herein as compound 1, or compound 118A), persephacin B, and persephacin C. Persephacins A-C were tested against a panel of fungal species that are known to be plant pathogens using fludioxonil, anon-systematic fungicide used for agriculture purposes, as a positive control. The MIC, minimum inhibitory concentration or the amount required to reduce growth by 75%, and the MFC, minimum fungicidal concentration or the amount required to reduce growth by 100%, were determined against the 8 different isolates: *Alternaria brassicicola, Alternaria brassicae, Alternaria tennuissiema, Fusarium oxysporum, Fusarium tricinctum, Mycosphaerella populorum, Nodulosporium* spp and *Pfaffia gloerata*. In all cases, persephacin C did not achieve complete or even 75% inhibition in the tested ranges of 0.32 μM to 10 μM (Tables 4 and 5). This is consistent with published data on aureobasidins, similar cyclic peptide also with a 3-OH valine, that lost activity after synthetic modifications attached long chain aliphatic residues. Persephacin B had lower WC values than persephacin A for all fungi except the *M. populorium* and *P. glomerate* in which persephacin A had a lower MIC value and Nodulosporium where neither compound showed MIC or MFC activity in the designated range. The fludioxonil was more potent than the peptides, with lower MIC except in the cases of *F. oxysporum*, where it matched persephacin A, and persephacin B had a lower MIC (1.25 µM versus 5 µM), and *P. glomerata*, where fludioxonil had no activity in the range tested, whereas both persephacin A and B had low MIC (0.625, 1.25) and MFC (1.25, 5) values.

TABLE 4

MIC Values of Persephacin A-C and Fludioxonil Against Various Phytopathogenic (Endophytic) Fungi

| Fungal Species | Persephacin A | Persephacin B | Persephacin C | Fludioxonil |
|---|---|---|---|---|
| A. brassicicola | 5 | 2.5 | >20 | 1.25 |
| A. brassicae | 1.25 | .625 | >20 | .625 |
| A. tennuissiema | 10 | 2.5 | >20 | 1.25 |
| Fusarium oxysporum | 5 | 1.25 | >20 | 5 |
| F. tricinctum | 5 | 2.5 | >20 | 1.25 |
| M. populorum | 2.5 | 5 | >20 | 1.25 |
| Nodulosporium spp. | >20 | >20 | >20 | .625 |
| P. glomerata | .625 | 1.25 | >20 | >20 |

MIC is the minimum inhibitory concentration (µM) or the amount required to reduce growth by to 75%.

TABLE 5

MFC Values of Persephacin A-C and Fludioxonil Against Various Phytopathogenic (Endophytic) Fungi

| Fungal Species | Persephacin A | Persephacin B | Persephacin C | Fludioxonil |
|---|---|---|---|---|
| A. brassicicola | 20 | >20 | >20 | >20 |
| A. brassicae | 2.5 | 1.25 | >20 | 2.5 |
| A. tennuissiema | 10 | 2.5 | >20 | 1.25 |
| Fusarium oxysporum | 20 | 20 | >20 | >20 |
| F. tricinctum | 10 | >20 | >20 | >20 |
| M. populorum | 10 | >20 | >20 | >20 |
| Nodulosporium spp. | >20 | >20 | >20 | >20 |
| P. glomerata | 1.25 | 5 | >20 | >20 |

MFC is the minimum fungicidal concentration (µM) or the amount required to reduce growth by 100%

Comparison of the Activity of Persephacin (Compound 118A) and Clinically-Used Medicine The effect of fluconazole and natamycin on fungal infection in comparison to persephacin A (Compound 118A) was evaluated at clinical dosage. Compound 118A (0.1%, 1 mg/ml) and natamycin (5%, 50 mg/ml) inhibited the growth of a yeast (*C. albicans* SC5314), a fluconazole-resistant yeast strain (*C. albicans* SC5314 Flu$^R$), and a filamentous fungus (*Aspergillus fumigatus* NRRL5109) (Table 6). Fluconazole (2%, 20 mg/ml) did not inhibit the growth of fluconazole-resistant yeast strain or the filamentous fungus. The persephacin was effective at a much lower concentration than the natamycin.

TABLE 6

Antifungal Activity of Persephacin vs. Natamycin and Fluconazole

| CFU | Candida albicans SC5314 | C. albicans SC5314 Flu$^R$ | Aspergillus fumigatus NRRL5109 |
|---|---|---|---|
| 118A (0.1%, 1 mg/ml) | 0 | 0 | 0 |
| Natamycin (5%, 50 mg/ml) | 0 | 0 | 0 |
| Fluconazole, (2%, 20 mg/ml) | 13.7 ± 19.3 | 2.2 ± 0.9 × 10$^5$ | 2.0 ± 1.0 × 10$^4$ |
| Control | 1.8 ± 0.4 × 10$^7$ | 1.3 ± 0.4 × 10$^7$ | 6.1 ± 0.7 × 10$^7$ |

Effect of Persephacin (compound 118A) on fungal infection on cornea ex vivo model The yeast pathogens (*Candida albicans* SC5314 and *C. albicans* SC5314 Flu$^R$) were recovered in Yeast Extract-Peptone-Dextrose (YPD) medium at 35° C., 200 rpm for 16 h. After being washed with Phosphate-buffered saline (PBS), the yeast was diluted with DMEM/F-12(sigma)+10% FBS (GE Healthcare Life Sciences)+Penicillin-Streptomycin at 4×10$^7$ cell/mL. The fresh pig cornea (Pel-Freez Biologicals, AR) were maintained with 4 mL DMEM/F-12 with 10% FBS and PS medium in 6-well plates. After being cultured with 25 µL of the fungal pathogen at 37° C., 5% CO$_2$ for 1 h, the cornea was washed with medium briefly to remove the unattached fungus. For *Aspergillus fumigatus* NRRL5109, the strain was recovered on MEA plate at 35° C. for 3 days. One loop of spores was suspended in DMEM/F-12 with 10% FBS and PS medium, and 25 µL spores was inoculated onto the cornea. Persephacin and drugs were dissolved in 30% DMSO. Natamycin (AdooQ Bioscience, CA) and fluconazole (Technology Catalysts International, VA) were used as positive controls. The cornea was treated with 504 compound and cultured at 37° C., 5% CO$_2$. After incubating for four days, the cornea images were obtained on a Leica DMS1000 microscope. All experiments were performed in triplicate, and example images are provided, as described below.

Figure 8:
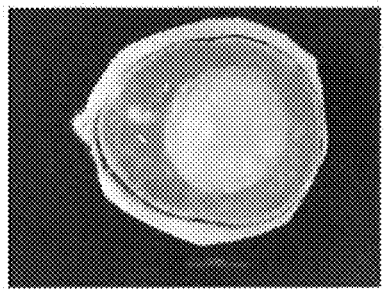
FIG. 8 shows the effect of different doses of compound 118A (persephacin) on *Candida albicans* (strain SC5314) growth in an ex vivo model of fungal keratitis. Porcine corneas were infected with the fungus and then treated with the compound at the listed concentrations (50-1,000 µg/mL). Persephacin was shown to be effective at reducing or eliminating the fungus at these concentrations.
Figure 8:
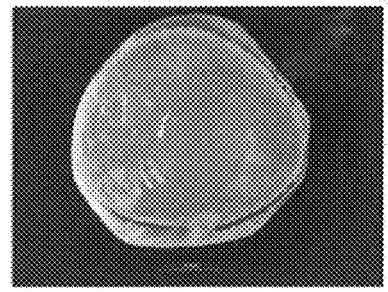
Figure 8:
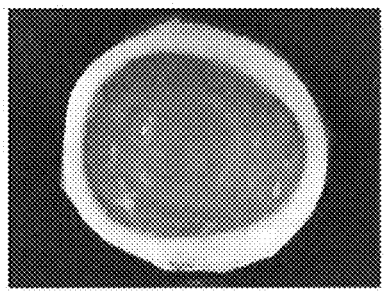
Figure 8:
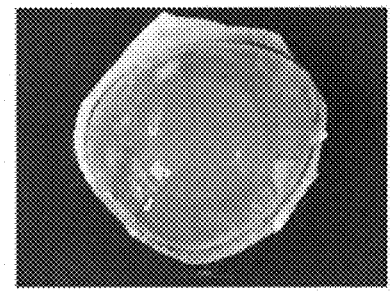
Figure 8:
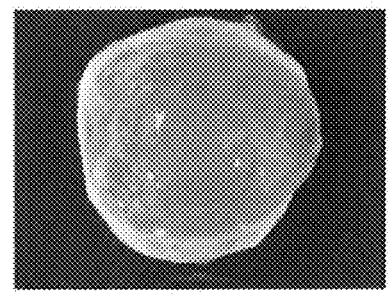

FIG. 8 shows the effect of different doses of compound 118A (persephacin A) on *Candida albicans* (strain SC5314) growth in an ex vivo model of fungal keratitis. Porcine corneas were infected with the fungus and then treated with the compound at the listed concentrations (50-1,000 µg/mL). Persephacin was shown to be effective at reducing or eliminating the fungus at these concentrations.

Figure 9:
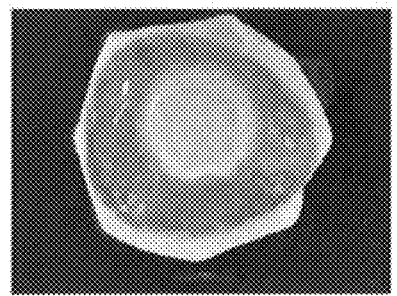
FIG. 9 shows the effect of different doses of 118A on *Candida albicans* (strain SC5314FluR, a fungus that is resistant to azole antifungal drugs) growth in an ex vivo model of fungal keratitis. Porcine corneas were infected with the fungus and then treated with the compound at the listed concentrations (50-1,000 µg/mL). Persephacin was shown to be effective at reducing or eliminating the fungus at these concentrations.
Figure 9:
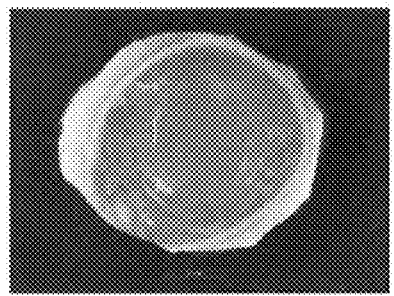
Figure 9:
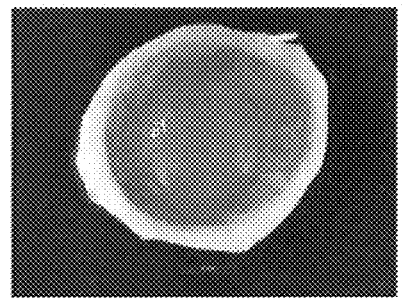
Figure 9:
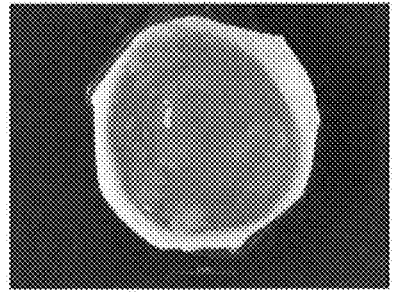
Figure 9:
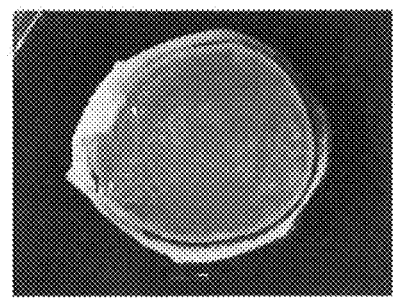

FIG. 9 shows the effect of different doses of compound 118A on *Candida albicans* (strain SC5314FluR, a fungus that is resistant to azole antifungal drugs) growth in an ex vivo model of fungal keratitis. Porcine corneas were infected with the fungus and then treated with the compound at the listed concentrations (50-1,000 µg/mL). Persephacin was shown to be effective at reducing or eliminating the fungus at these concentrations.

Figure 10:
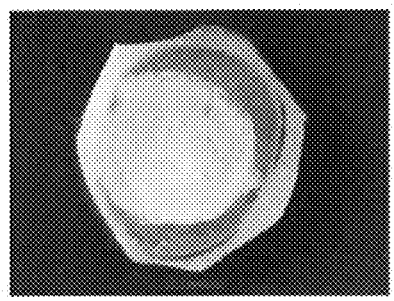
FIG. 10 shows the effect of different doses of 118A on *Aspergillus fumigatus* (strain NRRL 5109) growth in an ex vivo model of fungal keratitis. Porcine corneas were infected with the fungus and then treated with the compound at the listed concentrations (50-1,000 µg/mL). Persephacin was shown to be effective at reducing (50-250 µg/mL) or eliminating (1,000 µg/mL) the fungus at these concentrations.
Figure 10:
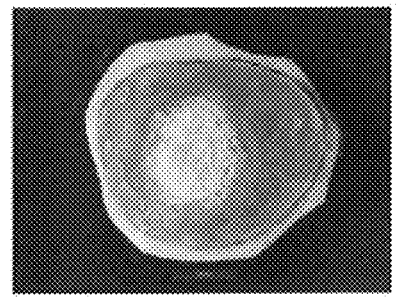
Figure 10:
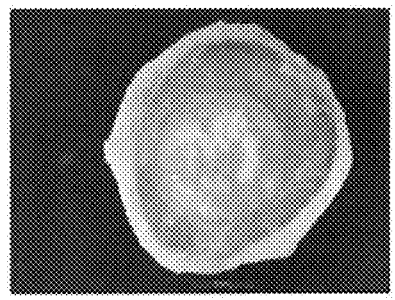
Figure 10:
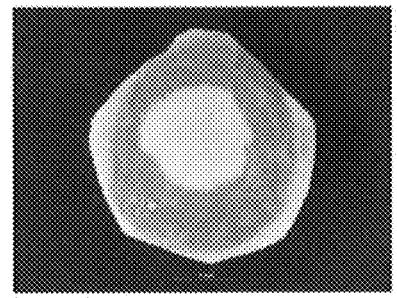
Figure 10:
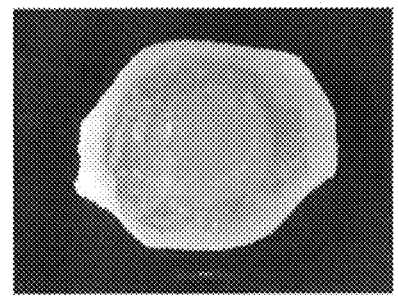

FIG. 10 shows the effect of different doses of compound 118A on *Aspergillus fumigatus* (strain NRRL 5109) growth in an ex vivo model of fungal keratitis. Porcine corneas were infected with the fungus and then treated with the compound at the listed concentrations (50-1,000 µg/mL). Persephacin was shown to be effective at reducing (50-250 µg/mL) or eliminating (1,000 µg/mL) the fungus at these concentrations.

Figure 11:
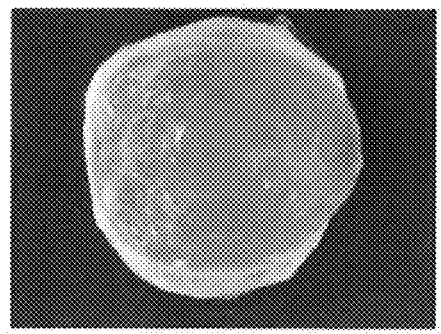
FIG. 11 shows a comparison of the antifungal activities of 0.1% 118A, 2% fluconazole, and 5% natamycin against *Candida albicans* (strain SC5314) in an ex vivo model of fungal keratitis. The fluconazole and natamycin concentration were selected as representative of clinically prescribed standard of care conditions. While all compounds reduced the infection, results showed that persephacin eliminated the fungus at a much lower concentration compared to currently used FDA-approved (natamycin) and off-label (fluconazole) clinical agents.
Figure 11:
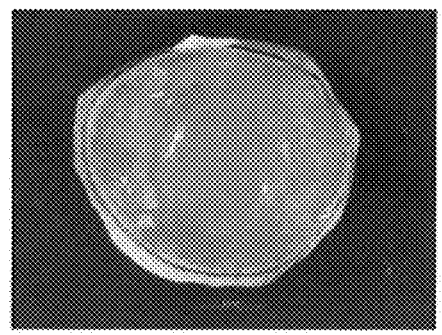
Figure 11:
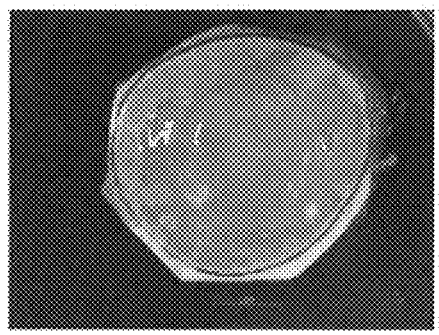
Figure 11:
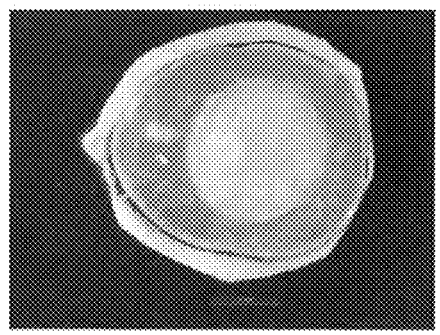

FIG. 11 shows a comparison of the antifungal activities of 0.1% compound 118A, 2% fluconazole, and 5% natamycin against *Candida albicans* (strain SC5314) in an ex vivo model of fungal keratitis. The fluconazole and natamycin concentrations were selected as representative of clinically prescribed standard of care conditions. While all compounds reduced the infection, results showed that persephacin eliminated the fungus at a much lower concentration compared to currently used FDA-approved (natamycin) and off-label (fluconazole) clinical agents.

Figure 12:
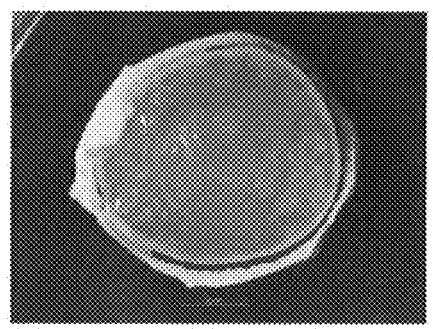
FIG. 12 shows a comparison of the antifungal activities of 0.1% 118A, 2% fluconazole, and 5% natamycin against *Candida albicans* (strain SC5314FluR, a fungus that is resistant to azole antifungal drugs) in an ex vivo model of fungal keratitis. The fluconazole and natamycin concentration were selected as representative of clinically prescribed standard of care conditions. Whereas natamycin reduced the fungal burden, fluconazole was unable to inhibit the fungus. Persephacin eliminated the fungus at a much lower concentration compared to currently used FDA-approved (natamycin) and off-label (fluconazole) clinical agents.
Figure 12:
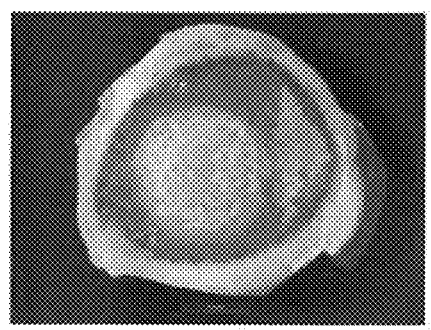
Figure 12:
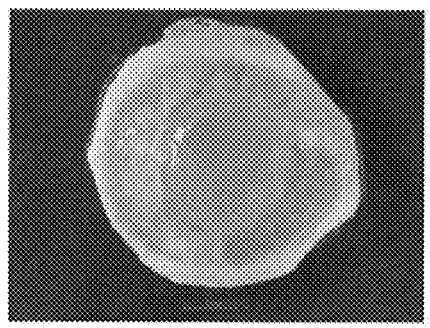
Figure 12:
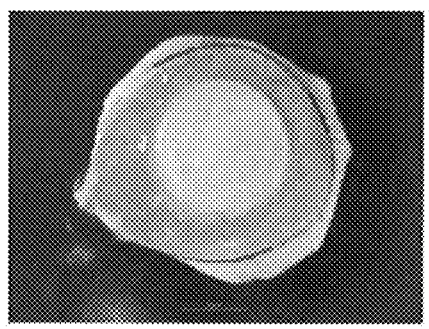

FIG. 12 shows a comparison of the antifungal activities of 0.1% compound 118A, 2% fluconazole, and 5% natamycin against *Candida albicans* (strain SC5314FluR, a fungus that is resistant to azole antifungal drugs) in an ex vivo model of fungal keratitis. The fluconazole and natamycin concentrations were selected as representative of clinically prescribed standard of care conditions. Whereas natamycin reduced the fungal burden, fluconazole was unable to inhibit the fungus. Persephacin eliminated the fungus at a much lower concentration compared to currently used FDA-approved (natamycin) and off-label (fluconazole) clinical agents.

Figure 13:
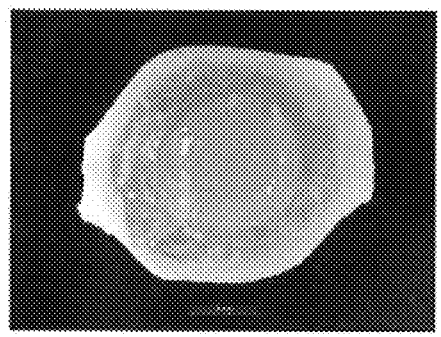
FIG. 13 shows a comparison of the antifungal activities of 0.1% 118A, 2% fluconazole, and 5% natamycin against *Aspergillus fumigatus* (strain NRRL 5109) in an ex vivo model of fungal keratitis. The fluconazole and natamycin concentration were selected as representative of clinically prescribed standard of care conditions. Whereas natamycin reduced the fungal burden, fluconazole was unable to fully inhibit the fungus. Persephacin eliminated the fungus at a much lower concentration compared to currently used FDA-approved (natamycin) and off-label (fluconazole) clinical agents.
Figure 13:
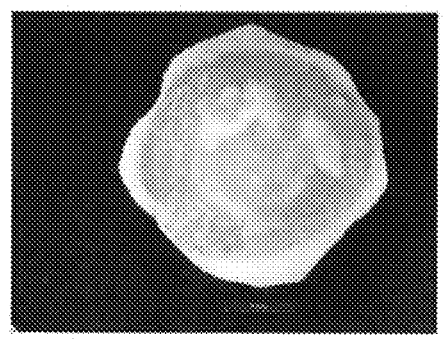
Figure 13:
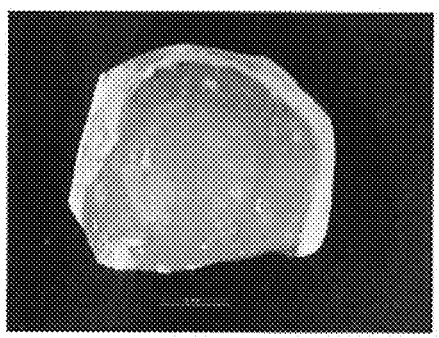
Figure 13:
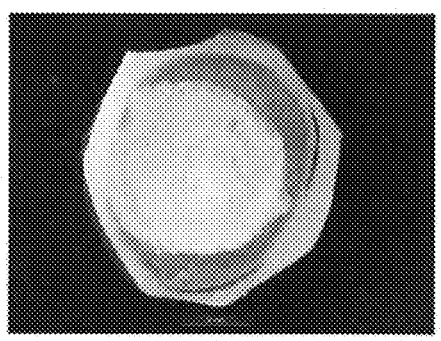

FIG. 13 shows a comparison of the antifungal activities of 0.1% compound 118A, 2% fluconazole, and 5% natamycin against *Aspergillus fumigatus* (strain NRRL 5109) in an ex vivo model of fungal keratitis. The fluconazole and natamycin concentrations were selected as representative of clinically prescribed standard of care conditions. Whereas natamycin reduced the fungal burden, fluconazole was unable to fully inhibit the fungus. Persephacin eliminated the fungus at a much lower concentration compared to currently used FDA-approved (natamycin) and off-label (fluconazole) clinical agents.

Thus, in accordance with the present disclosure, there have been provided compositions and methods of producing and using same which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. A method of treating a fungal infection in a subject in need of such treatment, wherein the method comprises:
   administering to the subject a compound comprising Formula II or a stereoisomer thereof:

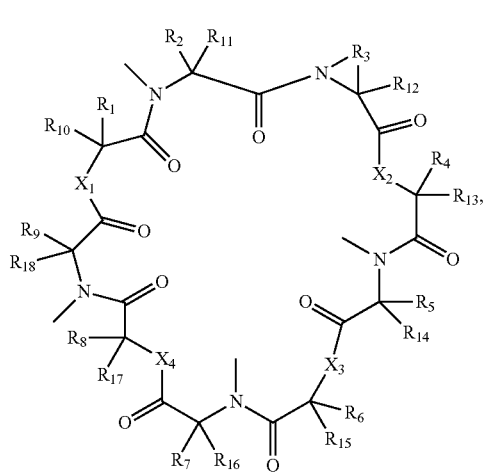

wherein:
$X_1$ is NH;
$X_2$ is NH;
$X_3$ is NH;
$X_4$ is O;
$R_1$ is selected from the group consisting of a side chain of persaphanine and structural and optical isomers thereof, wherein persephanine has the structure:

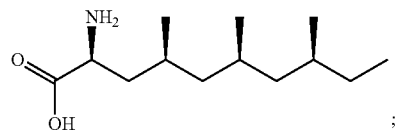 [SMILES: CC[C@H](C)C[C@H](C)C[C@H](C)C[C@H](N)C(=O)O]

$R_2$ is selected from the group consisting of hydrogen (H), deuterium (D), methyl, ethyl, linear or branched $C_3$-$C_{20}$ alkyl, a side chain of amino acid, a linear or branched $C_3$-$C_{20}$ alkenyl, and a linear or branched $C_2$-$C_{20}$ alkynyl;

$R_3$ is selected from the group consisting of alkyl or branched $C_1$-$C_6$ alkyl, $C_1$-$C_6$ alkyl ether, and $C_1$-$C_6$ alkyl amine;

$R_4$, $R_5$, $R_6$, $R_8$, $R_9$ are independently selected from the group consisting of straight chain or branched $C_1$-$C_5$ alkyl, straight chain or branched $C_1$-$C_5$ alkenyl, straight chain or branched $C_1$-$C_5$ alkynyl, straight chain or branched $C_1$-$C_5$ alkyl halide, straight chain or branched $C_1$-$C_5$ alkenyl halide, straight chain or branched $C_1$-$C_5$ alkynyl halide, straight chain or branched $C_1$-$C_5$ alkyl amine, straight chain or branched $C_1$-$C_5$ alkenyl amine, straight chain or branched $C_1$-$C_5$ alkynyl amine, straight chain or branched $C_1$-$C_5$ alkyl alcohol, straight chain or branched $C_1$-$C_5$ alkenyl alcohol, straight chain or branched $C_1$-$C_5$ alkynyl alcohol, straight chain or branched $C_1$-$C_5$ alkyl ether, straight chain or branched $C_1$-$C_5$ alkenyl ether, straight chain or branched $C_1$-$C_5$ alkynyl ether, straight chain or branched $C_1$-$C_5$ alkyl thiol, straight chain or branched $C_1$-$C_5$ alkenyl thiol, straight chain or branched $C_1$-$C_5$ alkynyl thiol, straight chain or branched $C_1$-$C_5$ alkyl sulfide, straight chain or branched $C_1$-$C_5$ alkenyl sulfide, straight chain or branched $C_1$-$C_5$ alkynyl sulfide, straight chain or branched $C_1$-$C_5$ alkyl sulfoxide, straight chain or branched $C_1$-$C_5$ alkenyl sulfoxide, straight chain or branched $C_1$-$C_5$ alkynyl sulfoxide, straight chain or branched $C_1$-$C_5$ alkyl sulfone, straight chain or branched $C_1$-$C_5$ alkenyl sulfone, straight chain or branched $C_1$-$C_5$ alkynyl sulfone, straight chain or branched $C_1$-$C_5$ alkyl nitrile, straight chain or branched $C_1$-$C_5$ alkenyl nitrile, straight chain or branched $C_1$-$C_5$ alkynyl nitrile, straight chain or branched $C_1$-$C_5$ alkyl isonitrile, straight chain or branched $C_1$-$C_5$ alkenyl isonitrile, straight chain or branched $C_1$-$C_5$ alkynyl isonitrile, straight chain or branched $C_1$-$C_5$ alkyl nitrite, straight chain or branched $C_1$-$C_5$ alkenyl nitrite, straight chain or branched $C_1$-$C_5$ alkynyl nitrite, straight chain or branched $C_1$-$C_5$ alkyl oxime, straight chain or branched $C_1$-$C_5$ alkenyl oxime, straight chain or branched $C_1$-$C_5$ alkynyl oxime, straight chain or branched $C_1$-$C_5$ alkyl nitroso, straight chain or branched $C_1$-$C_5$ alkenyl nitroso, straight chain or branched $C_1$-$C_5$ alkynyl nitroso, straight chain or branched $C_1$-$C_5$ alkyl nitro, straight chain or branched $C_1$-$C_5$ alkenyl nitro, straight chain or branched $C_1$-$C_5$ alkynyl nitro, straight chain or branched $C_1$-$C_5$ alkyl nitrate, straight chain or branched $C_1$-$C_5$ alkenyl nitrate, straight chain or branched $C_1$-$C_5$ alkynyl nitrate, straight chain or branched $C_1$-$C_5$ alkyl imide, straight chain or branched $C_1$-$C_5$ alkenyl imide, straight chain or branched $C_1$-$C_5$ alkynyl imide, straight chain or branched $C_1$-$C_5$ alkyl imine, straight chain or branched $C_1$-$C_5$ alkenyl imine, straight chain or branched $C_1$-$C_5$ alkynyl imine, straight chain or branched $C_1$-$C_5$ alkyl amide, straight chain or branched $C_1$-$C_5$ alkenyl amide, straight chain or branched $C_1$-$C_5$ alkynyl amide, straight chain or branched $C_1$-$C_5$ alkyl ester, straight chain or branched $C_1$-$C_5$ alkenyl ester, straight chain or branched $C_1$-$C_5$ alkynyl ester, straight chain or branched $C_1$-$C_5$ alkyl ketone, straight chain or branched $C_1$-$C_5$ alkenyl ketone, straight chain or branched $C_1$-$C_5$ alkynyl ketone, straight chain or branched $C_1$-$C_5$ alkyl carbonate, straight chain or branched $C_1$-$C_5$ alkenyl carbonate, straight chain or branched $C_1$-$C_5$ alkynyl carbonate, straight chain or branched $C_1$-$C_5$ (cyclopropyl)alkyl, straight chain or branched $C_1$-$C_5$ (cyclopropyl)alkenyl, straight chain or branched $C_1$-$C_5$ (cyclopropyl)alkynyl, straight chain or branched $C_1$-$C_5$ (cyclobutyl)alkyl, straight chain or branched $C_1$-$C_5$ (cyclobutyl)alkenyl, straight chain or branched $C_1$-$C_5$ (cyclobutyl)alkynyl, straight chain or branched $C_1$-$C_5$ alkyl silane, straight chain or branched $C_1$-$C_5$ alkenyl silane, straight chain or branched $C_1$-$C_5$ alkynyl silane, straight chain or branched $C_1$-$C_5$ alkyl, straight chain or branched $C_1$-$C_5$ alkynyl, methyl, ethyl, propyl, butyl, methyl imidazole, butyl amine, propyl guanidine, methyl-1-ol, ethyl-2-ol, ethyl-1-ol, ethyloic acid, propanoic acid, carboxymethyl, carboxyethyl, ethylamide, propylamide, methyl-1-thiol, ethyl-1-thiol, methyl sulfane, ethyl sulfane, isobutyl, sec-butyl, Cert-butyl, and isopropyl;

$R_7$ is selected from the group consisting of straight chain or branched $C_1$-$C_5$ alkyl alcohol, straight chain or branched $C_1$-$C_5$ alkenyl alcohol, straight chain or branched $C_1$-$C_5$ alkynyl alcohol, straight chain or branched $C_1$-$C_5$ alkyl amine, straight chain or branched $C_1$-$C_5$ alkenyl amine, straight chain or branched $C_1$-$C_5$ alkynyl amine, straight chain or branched $C_1$-$C_5$ alkyl thiol, straight chain or branched $C_1$-$C_5$ alkenyl thiol, and straight chain or branched $C_1$-$C_5$ alkynyl thiol; and $R_{10}$, $R_{11}$, $R_{12}$, $R_{13}$, $R_{14}$, $R_{15}$, $R_{16}$, $R_{17}$ and $R_{18}$ are independently selected from the group consisting of H, D, linear or branched $C_1$-$C_5$ alkyl, methyl, and ethyl.

2. The method of claim 1, wherein the fungal infection is an ocular fungal infection and the compound is topically administered.

3. The method of claim 1, wherein the compound comprising Formula II is:

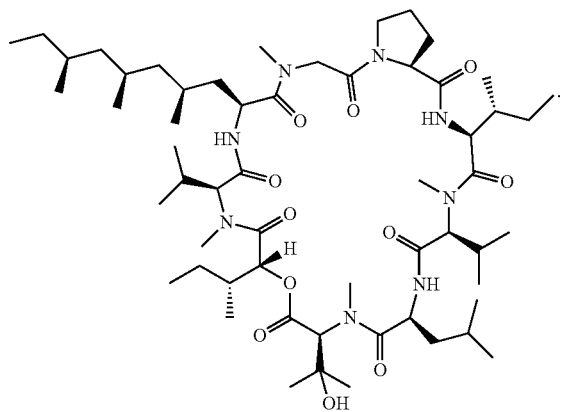 [SMILES: CC[C@H](C)C[C@H](C)C[C@H](C)C[C@@H]1NC(=O)[C@H](C(C)C)N(C)C(=O)[C@@H]([C@H](C)CC)OC(=O)[C@H](C(C)(C)O)N(C)C(=O)[C@H](CC(C)C)NC(=O)[C@H](C(C)C)N(C)C(=O)[C@H]([C@H](C)CC)NC(=O)[C@@H]2CCCN2C(=O)CN(C)C1=O]

* * * * *

UNITED STATES PATENT AND TRADEMARK OFFICE
CERTIFICATE OF CORRECTION

PATENT NO. : 11,643,438 B2
APPLICATION NO. : 17/260148
DATED : May 9, 2023
INVENTOR(S) : Robert H. Cichewicz et al.

It is certified that error appears in the above-identified patent and that said Letters Patent is hereby corrected as shown below:

In the Specification
Column 42, Line 35: After "treated with" delete "504" and replace with -- 50 µL --

In the Claims
Column 45, Line 36-37: Delete "Cert-butyl," and replace with -- tert-butyl --

Signed and Sealed this
Thirteenth Day of June, 2023

Katherine Kelly Vidal
*Director of the United States Patent and Trademark Office*